(12) United States Patent
McClure et al.

(10) Patent No.: US 7,801,602 B2
(45) Date of Patent: Sep. 21, 2010

(54) CONTROLLING STIMULATION PARAMETERS OF IMPLANTED TISSUE STIMULATORS

(75) Inventors: Kelly H. McClure, Simi Valley, CA (US); Rafael Carbunaru, Studio City, CA (US); George Vamos, Studio City, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1079 days.

(21) Appl. No.: 11/388,836

(22) Filed: Mar. 24, 2006

(65) Prior Publication Data
US 2006/0229688 A1 Oct. 12, 2006

Related U.S. Application Data

(60) Provisional application No. 60/669,822, filed on Apr. 8, 2005.

(51) Int. Cl.
*A61N 1/00* (2006.01)
(52) U.S. Cl. .......................................................... 607/2
(58) Field of Classification Search ................. 600/544, 600/510; 607/3, 9, 41, 197, 46, 2, 118, 378, 607/45, 34, 44, 72, 60
See application file for complete search history.

(56) References Cited

U.S. PATENT DOCUMENTS

| | | | |
|---|---|---|---|
| 3,850,161 A | 11/1974 | Liss | 600/544 |
| 3,881,495 A | 5/1975 | Pannozzo et al. | 607/55 |
| 4,232,679 A | 11/1980 | Schulman | 607/33 |
| 4,408,608 A | 10/1983 | Daly et al. | 607/57 |
| 4,481,950 A | 11/1984 | Duggan | 607/29 |
| 4,590,946 A | 5/1986 | Loeb | 600/375 |
| 4,608,985 A | 9/1986 | Crish et al. | 607/74 |
| 4,628,942 A | 12/1986 | Sweeney et al. | 607/118 |
| 4,649,936 A | 3/1987 | Ungar et al. | 607/118 |
| 4,702,254 A | 10/1987 | Zabara | 607/45 |
| 4,793,353 A | 12/1988 | Borkan | |
| 5,188,104 A | 2/1993 | Wernicke et al. | 607/40 |
| 5,215,086 A | 6/1993 | Terry, Jr. et al. | 607/46 |

(Continued)

FOREIGN PATENT DOCUMENTS

WO PCT/US2005/040688 11/2005

(Continued)

OTHER PUBLICATIONS

U.S. Appl. No. 10/179,010, filed Jun. 20, 2002.

(Continued)

*Primary Examiner*—George Manuel
*Assistant Examiner*—Robert N Wieland
(74) *Attorney, Agent, or Firm*—Vista IP Law Group LLP

(57) ABSTRACT

Systems and techniques for controlling the stimulation of tissue. In one aspect, an apparatus includes an implantable stimulation device to elicit a response in a tissue by delivering one or more stimuli. The stimulation device includes a stimulus delivery element to deliver the one or more stimuli to elicit the response, a memory to store a range value identifying a range of values of a stimulation parameter relative to a first value, and a controller to control delivery of the stimuli by the stimulus delivery element in accordance with the range value. The stimulation parameter characterizes the stimuli to be delivered by the stimulation device.

32 Claims, 12 Drawing Sheets

U.S. PATENT DOCUMENTS

| | | | |
|---|---|---|---|
| 5,222,494 A * | 6/1993 | Baker, Jr. | 607/118 |
| 5,299,569 A | 4/1994 | Wernicke et al. | 607/45 |
| 5,305,445 A | 4/1994 | Nishikawa | 711/2 |
| 5,305,745 A | 4/1994 | Zacouto | 600/324 |
| 5,314,458 A | 5/1994 | Najafi et al. | 607/116 |
| 5,330,515 A | 7/1994 | Rutecki et al. | 607/46 |
| 5,358,514 A | 10/1994 | Schulman et al. | 607/61 |
| 5,576,486 A * | 11/1996 | Paz | 73/197 |
| 5,700,282 A | 12/1997 | Zabara | 607/9 |
| 5,716,318 A | 2/1998 | Manning | 600/16 |
| 5,752,979 A | 5/1998 | Benabid | 607/72 |
| 5,755,750 A | 5/1998 | Petruska et al. | 607/75 |
| 5,895,416 A | 4/1999 | Barreras et al. | 607/62 |
| 5,995,868 A | 11/1999 | Dorfmeister et al. | 600/544 |
| 6,104,956 A | 8/2000 | Naritoku et al. | 607/45 |
| 6,112,116 A | 8/2000 | Fischell et al. | 600/517 |
| 6,154,678 A | 11/2000 | Lauro | |
| 6,178,349 B1 | 1/2001 | Kieval | 607/3 |
| 6,205,359 B1 | 3/2001 | Boveja | 607/45 |
| 6,216,045 B1 | 4/2001 | Black et al. | |
| 6,266,564 B1 | 7/2001 | Hill et al. | 607/9 |
| 6,341,236 B1 | 1/2002 | Osorio et al. | 607/45 |
| 6,393,325 B1 * | 5/2002 | Mann et al. | 607/46 |
| 6,526,318 B1 | 2/2003 | Ansarinia | 607/46 |
| 6,560,490 B2 | 5/2003 | Grill et al. | 607/72 |
| 6,597,954 B1 | 7/2003 | Pless et al. | 607/62 |
| 6,712,753 B2 | 3/2004 | Manne | 600/9 |
| 6,782,292 B2 | 8/2004 | Whitehurst | 607/45 |
| 6,810,285 B2 * | 10/2004 | Pless et al. | 600/544 |
| 6,826,428 B1 | 11/2004 | Chen et al. | 607/40 |
| 6,907,295 B2 | 6/2005 | Gross et al. | 607/118 |
| 6,928,320 B2 | 8/2005 | King | 607/5 |
| 2001/0003799 A1 | 6/2001 | Boveja | 607/45 |
| 2002/0016615 A1 | 2/2002 | Dev et al. | |
| 2002/0022873 A1 | 2/2002 | Erickson et al. | 607/117 |
| 2003/0036773 A1 * | 2/2003 | Whitehurst et al. | 607/3 |
| 2003/0083698 A1 | 5/2003 | Whitehurst et al. | 607/3 |
| 2003/0203890 A1 | 10/2003 | Steiner et al. | 514/211.01 |
| 2003/0236557 A1 | 12/2003 | Whitehurst et al. | 607/39 |
| 2003/0236558 A1 | 12/2003 | Whitehurst et al. | 607/45 |
| 2004/0015204 A1 | 1/2004 | Whitehurst et al. | 607/48 |
| 2004/0015205 A1 | 1/2004 | Whitehurst et al. | 607/48 |
| 2004/0172089 A1 | 9/2004 | Whitehurst et al. | 607/45 |
| 2004/0243182 A1 | 12/2004 | Cohen et al. | 607/2 |
| 2005/0101878 A1 | 5/2005 | Daly et al. | 600/559 |
| 2005/0245971 A1 | 11/2005 | Brockway et al. | 607/2 |
| 2006/0173493 A1 * | 8/2006 | Armstrong et al. | 607/2 |
| 2006/0195154 A1 * | 8/2006 | Jaax et al. | 607/45 |
| 2007/0299477 A1 * | 12/2007 | Kleckner et al. | 607/9 |
| 2009/0163975 A1 * | 6/2009 | Gerber et al. | 607/41 |
| 2009/0253977 A1 * | 10/2009 | Kipke et al. | 600/378 |

FOREIGN PATENT DOCUMENTS

WO  PCT/US2006/034652  9/2006

OTHER PUBLICATIONS

U.S. Appl. No. 10/176,722, filed Jun. 20, 2002.
U.S. Appl. No. 10/176,743, filed Jun. 20, 2002.
U.S. Appl. No. 10/178,011, filed Jun. 20, 2002.
U.S. Appl. No. 10/285,803, filed Nov. 1, 2002.
U.S. Appl. No. 10/982,371, filed Nov. 5, 2004.
U.S. Appl. No. 10/981,944, filed Nov. 5, 2004.
U.S. Appl. No. 10/992,625, filed Nov. 17, 2004.
U.S. Appl. No. 10/992,390, filed Nov. 17, 2004.
U.S. Appl. No. 11/003,155, filed Dec. 3, 2004.
U.S. Appl. No. 11/008,869, filed Dec. 9, 2004.
U.S. Appl. No. 11/016,604, filed Dec. 16, 2004.
U.S. Appl. No. 11/089,171, filed Mar. 24, 2005.
U.S. Appl. No. 11/122,648, filed May 5, 2005.
U.S. Appl. No. 11/130,644, filed May 16, 2005.
U.S. Appl. No. 11/139,296, filed May 26, 2005.
U.S. Appl. No. 11/178,054, filed Jul. 8, 2005.
U.S. Appl. No. 11/221,095, filed Sep. 6, 2005.
U.S. Appl. No. 11/226,777, filed Sep. 13, 2005.
U.S. Appl. No. 11/261,432, filed Oct. 28, 2005.
U.S. Appl. No. 11/262,055, filed Oct. 28, 2005.
U.S. Appl. No. 11/291,464, filed Nov. 30, 2005.
U.S. Appl. No. 11/386,198, filed Mar. 21, 2006.
U.S. Appl. No. 11/387,206, filed Mar. 23, 2006.
U.S. Appl. No. 11/418,847, filed May 5, 2006.
U.S. Appl. No. 11/536,565, filed Sep. 28, 2006.

* cited by examiner

CONTROLLING STIMULATION PARAMETERS OF IMPLANTED TISSUE STIMULATORS

CROSS-REFERENCE TO RELATED APPLICATIONS

This application claims priority to U.S. Provisional Application Ser. No. 60/669,822, filed on Apr. 8, 2005, the contents of which are incorporated herein as reference.

BACKGROUND

This disclosure relates to controlling stimulation parameters of implanted tissue stimulators.

Tissues can be stimulated directly or indirectly to elicit a desired response. Direct stimulation involves the provision of one or more stimuli directly to the stimulated tissue. Indirect stimulation involves the provision of one or more stimuli to adjacent or otherwise related tissue, where the related tissue causes the desired response to be elicited from the stimulated tissue. The desired response can be inhibitory or excitatory. Inhibitory responses tend to discourage certain behavior by the stimulated tissue, whereas excitatory responses tend to encourage certain behavior by the stimulated tissue. Encouraged or discouraged behaviors can include cellular depolarization, the release of chemical species, and/or the inhibition of cellular depolarization.

Tissue can be stimulated, e.g., using electrical, chemical, thermal, electromagnetic, and/or mechanical stimuli. Stimuli can be used by medical devices to stimulate tissue in a number of different settings, including therapeutic, diagnostic, and functional settings. In such settings, stimulation is often provided in accordance with stimulation parameters. The stimulation parameters characterize the stimuli for purposes of delivery.

SUMMARY

Systems and techniques for controlling the stimulation of tissue are described. In one aspect, an apparatus includes an implantable stimulation device to elicit a response in a tissue by delivering one or more stimuli. The stimulation device includes a stimulus delivery element to deliver the one or more stimuli to elicit the response, a memory to store a range value identifying a range of values of a stimulation parameter relative to a first value, and a controller to control delivery of the stimuli by the stimulus delivery element in accordance with the range value. The stimulation parameter characterizes the stimuli to be delivered by the stimulation device.

This and other aspects can include one or more of the following features. The first value can be a default value of the stimulation parameter. The range value can identify the range of values by identifying a range of excluded values of the stimulation parameter. The range of values can be a range of allowable values of the stimulation parameter. The range of values can be a group of discrete allowable values of the stimulation parameter. The first value can be a midpoint of the range identified by the range value. The first value can be a boundary of the range identified by the range value.

The stimulation parameter can characterizes an electrical signal or a bolus of chemical delivered to stimulate the tissue. For example, the stimulation parameter can characterize one or more of a primary pulse amplitude, a primary pulse duration, a delay between a primary pulse and a secondary pulse, a secondary pulse amplitude, a secondary pulse duration, a period, a primary pulse shape, and a secondary pulse shape. The stimulus delivery element can be an electrode to deliver electrical stimuli to elicit the response.

The stimulus delivery element can be a drug delivery device to deliver a chemical stimulus to elicit the response. The controller can include a data processing device to control the delivery of the one or more stimuli in accordance with logic of a set of machine-readable instructions. The apparatus can also include a data receiver to receive data from an extracorporeal portion. The received data can include the range value stored at the memory.

In another aspect, an apparatus can include an implantable stimulation device configured to deliver one or more stimuli to elicit a response from a tissue. The stimulation device can include a stimulus delivery element configured to deliver the one or more stimuli to elicit the response, a transceiver configured to exchange data with an extracorporeal device, a controller configured to control delivery of the one or more stimuli by the stimulus delivery element in light of the data exchanged with the extracorporeal device, and a hardware limiter configured to limit a range of a characteristic of the one or more stimuli to be delivered by the stimulus delivery element independently of the controller.

This and other aspects can include one or more of the following features. The hardware limiter can include a voltage limiter to limit a primary pulse voltage amplitude, a current limiter configured to limit a primary pulse current amplitude, a charge limiter configured to limit a charge delivered during a primary pulse, or a power limiter configured to limit a power delivered during a primary pulse. The hardware limiter can also include a dosage limiter configured to limit a dosage of a chemical delivered to stimulate a tissue. For example, a dosage limiter can include a flowmeter to measure the dosage delivered and generate a shut-off signal, and a valve to receive the shut-off signal and stop the delivery of the chemical.

In another aspect, a system for stimulating tissue can include an implanted portion and an extracorporeal portion. The implanted portion can include a stimulator configured to elicit a response from tissue using a stimulus and a data transmitter configured to transmit, over a data link, data regarding whether the stimulator is active. The extracorporeal portion can include a data receiver configured to receive the data from the implanted portion over the data link, a user interface configured to receive a proposed change to the stimulus from a user, and a processor configured to hinder the change to the stimulus when the data receiver receives data indicating that the stimulator is not currently active.

This and other aspects can include one or more of the following features. The extracorporeal portion can include logic to determine if the proposed change to the stimulus received from the user would increase the stimulation. The processor can be configured to reject the change to the stimulus when the data receiver receives data indicating that the stimulator is not active and the logic determines that the proposed change would increase the stimulation. The processor can also be configured to reject the change to the stimulus when the data receiver receives data indicating that the stimulator is not active.

In another aspect, a method includes receiving a stimulation adjustment at an extracorporeal portion of a system for stimulating tissue. At the extracorporeal portion, deciding whether the proposed stimulation adjustment is appropriate by determining if the proposed stimulation adjustment would yield a stimulation parameter outside a range of values of the stimulation parameter and, if the proposed stimulation adjustment is appropriate, determining a setting for the stimulation parameter based on the proposed stimulation adjustment and transmitting the stimulation parameter setting to the implanted stimulation device. At the implanted stimulation device, receiving the stimulation parameter setting from the extracorporeal portion. The stimulation adjustment proposes a change to one or more aspects of an stimulus to be delivered by an implanted stimulation device to elicit a response from a tissue. The stimulation parameter characterizes the stimulus to be delivered by the implanted stimulation device.

This and other aspects can include one or more of the following features. The proposed stimulation adjustment can be determined to be appropriate by retrieving a stored stimulation boundary from the implanted portion and determining if the proposed stimulation adjustment is within the boundary retrieved from the implanted portion.

The proposed stimulation adjustment can also be determined to be appropriate by accessing a range value identifying a range of values of a stimulation parameter relative to a first value and determining if the proposed stimulation adjustment is within the range identified by the range value. The stimulation parameter characterizes the stimulus to be delivered by the stimulation device. An incremental or decremental change to the stimulation parameter setting can be transmitted to the implanted stimulation device.

In another aspect, a method includes, at an extracorporeal portion of a system for delivering a stimulus to elicit a response from a tissue, comparing a stimulation parameter that would be yielded by a proposed adjustment to the stimulation parameter to a range of values of the stimulation parameter, determining, based on the comparison, that the proposed adjustment is inappropriate if the proposed adjustment would violate a boundary on the range of values, and accommodating the proposed stimulation adjustment by changing a setting of the stimulation parameter to the violated boundary. The stimulation parameter characterizes the electrical signal to be delivered by an implanted portion of the system.

This and other aspects can include one or more of the following features. The proposed stimulation adjustment can be accommodated by transmitting the setting of the stimulation parameter from the extracorporeal portion to the implanted portion or by incrementing or decrementing the setting of the stimulation parameter to the violated boundary. The proposed stimulation adjustment can also be accommodated by transmitting a revised stimulation adjustment from the extracorporeal portion to the implanted portion.

In another aspect, a method includes comparing a proposed adjustment to a stimulation parameter to a range of values of the stimulation parameter, determining, based on the comparison, that the proposed adjustment is inappropriate if the proposed adjustment would be outside the range of values of the stimulation parameter, and accommodating the inappropriate adjustment by rejecting the inappropriate adjustment to leave the stimulation parameter unchanged. The stimulation parameter characterizes a stimulus to be delivered by an implanted stimulation device to elicit a response from a tissue.

This and other aspects can include one or more of the following features. The range of values can be a range of allowable values of the stimulation parameter.

In another aspect, a method includes receiving, at an extracorporeal device, a proposed adjustment to a stimulus to be delivered by an implanted device, the stimulus to elicit a response from a tissue, determining whether the implanted device is active, and, if the implanted device is not active, rejecting the adjustment to leave the stimulus unchanged.

This and other aspects can include one or more of the following features. The adjustment can be rejected by determining whether the proposed adjustment would increase the stimulation provided by the stimulus, and, if the stimulation would be increased, rejecting the adjustment to leave the stimulus unchanged.

The details of one or more implementations are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Figure 1:
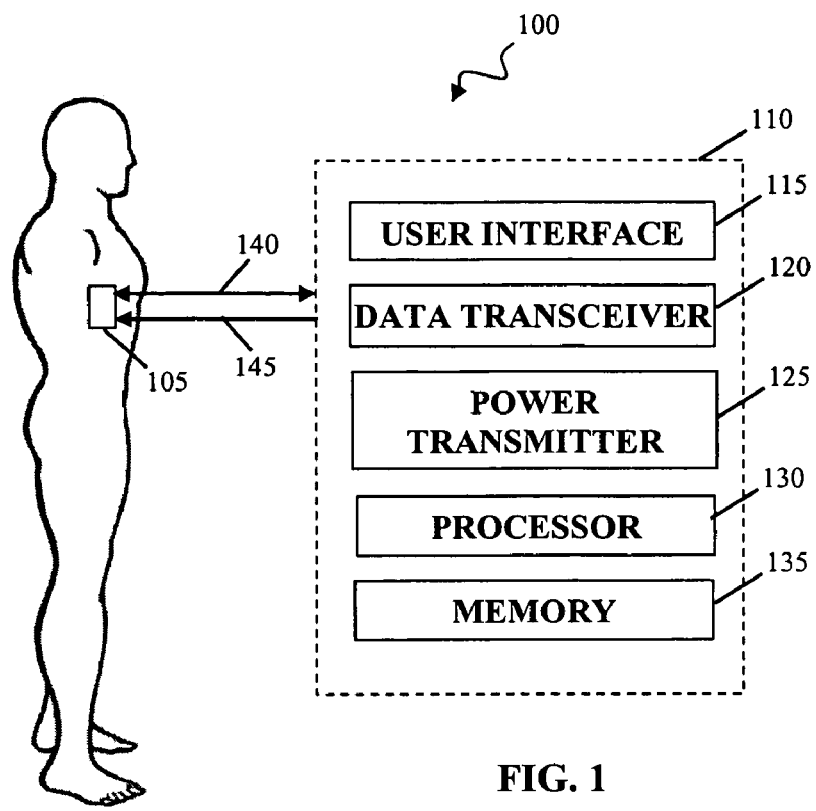
FIG. 1 shows a system for stimulating tissue.

FIG. 1 shows a system 100 for stimulating tissue. System 100 can stimulate tissue directly or indirectly to elicit a desired response. The desired response can be inhibitory or excitatory. System 100 can deliver one or more of, e.g., electrical stimuli, chemical stimuli, thermal stimuli, electromagnetic stimuli, and/or mechanical stimuli to elicit the desired response in any of a number of different settings.

System 100 can include an implanted portion 105 and an external (i.e., extracorporeal) portion 110. Implanted portion 105 is a device that is adapted for implantation in a body. For example, implanted portion 105 can include a biocompatible housing adapted to reduce the immune response and/or cell necrosis associated with the implantation of portion 105. Implanted portion 105 can stimulate tissue using one or more stimuli for therapeutic, diagnostic, and/or functional purposes. For example, implanted portion 105 can stimulate tissue by electrically exciting the depolarization of a nerve and/or muscle tissue. As another example, implanted portion 105 can stimulate tissue by delivering inhibitory chemical stimuli. As yet another example, implanted portion 105 can deliver light or other electromagnetic stimuli to stimulate photosensitive tissue. As discussed further below, implanted portion 105 can include one or more delivery elements to deliver stimuli to tissue. The delivery elements can include, e.g., electrodes, drug delivery elements, heaters, coolers, light sources, fiber optics, and/or mechanical elements such as piezoelectric elements, balloons, MEMS devices, and the like.

In some implementations, implanted portion 105 can be implanted in a body using one or more surgical insertion tools tailored for the implantation of portion 105. Alternatively, implanted portion 105 can be implanted using commercially available surgical equipment, such as hypodermic needles, conventional surgical equipment, and endoscopic or laparoscopic devices.

In some implementations, implanted portion 105 can operate independently (i.e., as a solitary implanted device) or implanted portion 105 can operate as part of an implanted system of devices whose activities are coordinated to achieve therapeutic, diagnostic, and/or functional purposes.

In some implementations, implanted portion 105 can receive data from one or more sensing devices (not shown) that respond to one or more conditions of the body in which implanted portion 105 is implanted. Example sensing devices include chemical sensors, electrodes, optical sensors, mechanical (e.g., motion, pressure) sensors, and temperature sensors. The received data can be used, alone or in conjunction with data received from external devices and/or other implanted devices, by implanted portion 105 in controlling the stimulation of tissue.

External (extracorporeal) portion 110 is a device for providing user interaction with implanted portion 105. External portion 110 is generally situated outside the body in which implanted portion 105 is implanted. External portion 110 can include a user interface 115, a data transceiver 120, a power transmitter 125, a processor 130, and a memory 135. User interface 115, data transceiver 120, power transmitter 125, processor 130, and memory 135 can be housed in a single housing or in multiple housings. User interface 115, data transceiver 120, power transmitter 125, processor 130, and memory 135 can be linked for data communication and control by one or more wired (e.g., wires, busses, optical fiber) or wireless (e.g., infrared, WiFi, radio frequency (RF)) data links.

User interface 115 can include one or more input/output devices for interacting with a user. For example, input/output devices can be mechanical, audio, and/or visual devices, including keypads, touch- and display-screens, speakers, and data ports.

Data transceiver 120 communicates with implanted portion 105 over a data link 140. This communication can include both the transmission and reception of data, including data that represents commands received from a user over user interface 115 and data regarding the operational status and history of implanted portion 105. For example, data that represents the boundaries on stimulation parameters, the current operational settings of stimulation parameters, and whether or not implanted portion 110 is currently stimulating tissue can be communicated over data link 140.

Data transceiver 120 includes a transmitter and a receiver. Data transceiver 120 can be a wireless transceiver in that transceiver 120 communicates with implanted portion 105 without the use of a transdermal physical link. For example, data transceiver 120 can communicate with implanted portion 105 using sound and/or electromagnetic radiation (e.g., light or radio waves) that propagates through a body to and from implanted portion 105.

Power transmitter 125 relays energy to implanted portion 105 over a power link 145. The energy relayed from transmitter 125 can be captured and stored in implanted portion 105 and subsequently converted into one or more stimuli for stimulating tissue. The relayed energy can include electrical energy, magnetic energy, electromagnetic energy, and/or mechanical energy. Power transmitter 125 can be a wireless transmitter in that transmitter 125 relays energy to implanted portion 105 without the use of a transdermal physical link.

Processor 130 is a data processing device that performs processing activities in accordance with logic established by a set of instructions. The instruction can be embodied in hardware and/or software. For example, the processor 130 can be a microprocessor, FPGA's, ASIC's, and/or a set of logic elements arranged to embody the instructions.

The instructions performed by processor 130 can implement operations associated with controlling the stimulation of tissue. These operations can include the management of interactions with a user over user interface 115, the communication of data with implanted portion 105 over data transceiver 120, and the relaying of energy to implanted portion 105 over power transmitter 125. These operations can also include various processes described below.

Memory 135 is a storage device that can store instructions and/or data for controlling the stimulation of tissue in machine-readable format. Memory 135 can be accessed by one or more of user interface 115, data transceiver 120, power transmitter 125, and processor 130 to store and/or retrieve instructions and/or data. Memory 135 can include a memory controller or other interface to facilitate such exchanges of information.

One class of data that can be stored in memory 135 is a stimulation parameter. A stimulation parameter characterizes the stimulation to be delivered by implanted portion 105. A stimulation parameter can characterize the stimulation to be delivered in a number of different ways. For example, a stimulation parameter can be a particular value (e.g., "15"), a reference to another value (e.g., "15 more than a reference value"), and/or a reference to a memory location or other discrete value (e.g., "the third element in the list [5, 10, 15, 20]"). Stimulation parameter can be identified using the values themselves (e.g., "the stimulation parameter is 5.0") or using comparisons (e.g., "the stimulation parameter is less than 5.0").

A stimulation parameter can characterize stimuli delivered by implanted portion 105 directly, or a stimulation parameter can characterize one or more aspects of the operation of implanted portion 105 that impacts the delivered stimuli. Examples of operational aspects that impact the delivered stimuli include the setting or calibration of a timer circuit or the selection of a particular power supply or stimulus delivery element (such as an electrode) when more that one is available.

Figure 2A:
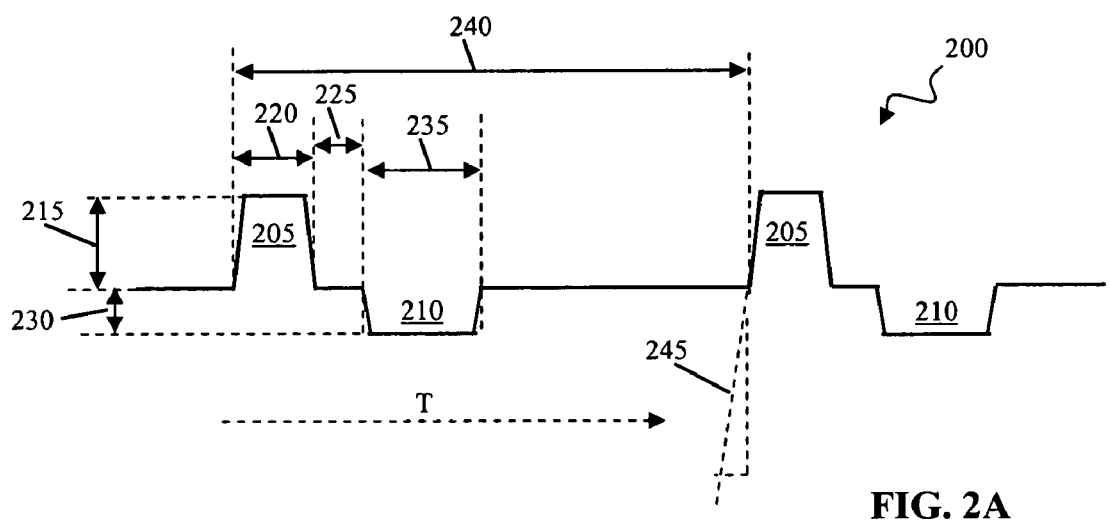
FIGS. 2A, 2B show example stimulation parameters that characterize a stimulus waveform.

FIG. 2A shows example stimulation parameters that characterize a stimulus waveform 200. Stimulus waveform 200 is an electrical signal that stimulates tissue by electrically exciting the depolarization of nerve and/or muscle tissue. Stimulus waveform 200 can be delivered by one or more electrodes in implanted portion 105.

Stimulus waveform 200 can represent either the voltage or the current of electrical stimuli as a function of time T. Stimulus waveform 200 can be a balanced-charge biphasic waveform in that substantial charge does not accumulate at the interface of an electrode that delivers stimulus waveform 200 and that corrosion of a delivery electrode is reduced. In one implementation, stimulus waveform 200 includes a repetitive series of alternating primary stimulation pulses 205 and secondary recovery pulses 210. Primary stimulation pulses 205 are electrical transients that are adapted to excite the depolarization of nerve and/or muscle tissue. Secondary recovery pulses 210 are electrical transients that are adapted to reduce the accumulation of charge at the electrode interface due to primary stimulation pulses 205.

In the illustrated implementation, stimulus waveform 200 is characterized by a primary pulse amplitude parameter 215, a primary pulse duration parameter 220, a delay parameter 225, a secondary pulse amplitude parameter 230, a secondary pulse duration parameter 235, a period parameter 240, and a pulse shape parameter 245.

Primary pulse amplitude parameter 215 characterizes either the voltage or current pulse amplitude of primary stimulation pulses 205 in waveform 200, whereas primary pulse duration parameter 220 characterizes the duration of primary stimulation pulses 205. Primary pulse amplitude parameter 215 is generally given in units of voltage or current, whereas primary pulse duration parameter 220 is generally given in units of time.

Delay parameter 225 characterizes the time between a primary pulse 205 and a secondary pulse 210. The time characterized by delay parameter 225 is generally long enough to prevent secondary pulses 210 from interfering with the depolarization of nerve and/or muscle tissue excited by primary pulses 205.

Secondary pulse amplitude parameter 230 characterizes either the voltage or current pulse amplitude of secondary recovery pulses 210 in waveform 200, whereas secondary pulse duration parameter 235 characterizes the duration of secondary recovery pulses 210. Secondary pulse amplitude parameter 230 is generally given in units of voltage or current, whereas secondary pulse duration parameter 235 is generally given in units of time.

Period parameter 240 characterizes the time between repetitions of identical portions of stimulus waveform 200. As illustrated, period parameter 240 characterizes the time between successive primary pulses 205 in waveform 200. Period parameter 240 can also be expressed as a pulse rate (e.g., pulses per time). Pulse shape parameter 245 characterizes an aspect of one or more pulses in waveform 200. As illustrated, pulse shape parameter 245 characterizes the rising slope of primary pulses 205, but a variety of other pulses and other aspects of pulses can be characterized by pulse shape parameters. For example, pulse shape parameter 245 can characterize a burst pattern or frequency content of a pulse.

Stimulus waveform 200 can be tailored to stimulate specific cell populations and exclude others from stimulation. For example, relatively low frequency electrical stimulation (e.g., less than about 50-100 Hz) may have an excitatory effect on adjacent neural tissue, leading to increased neural activity, whereas relatively high frequency electrical stimulation (e.g., greater than about 50-100 Hz) may have an inhibitory effect, leading to decreased neural activity. Similar tailoring can be used to stimulate and exclude other classes of tissues, such as muscle tissues.

Figure 2B:
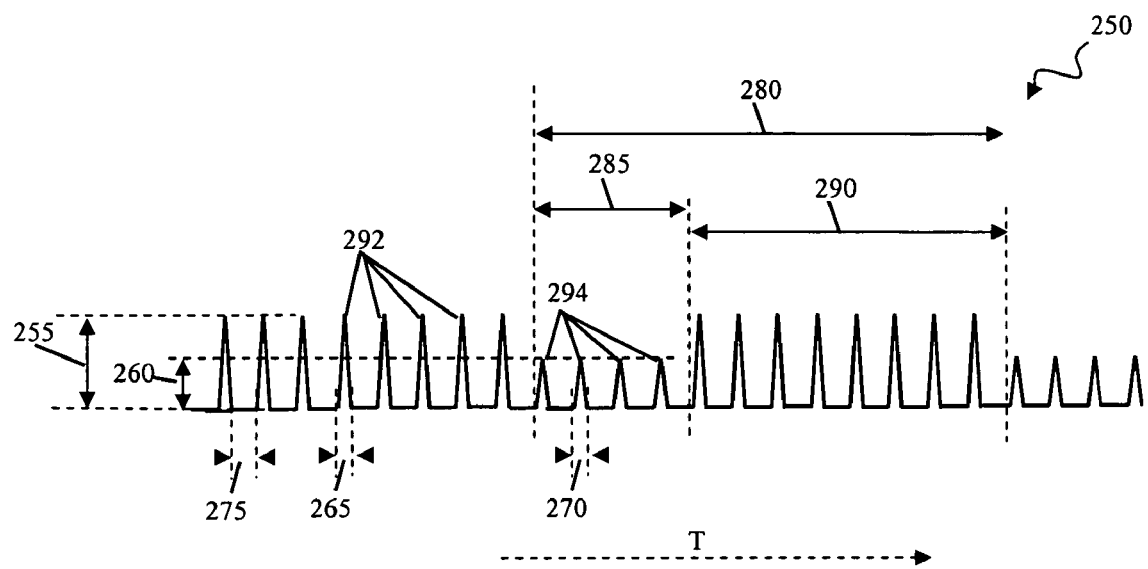

FIG. 2B shows example stimulation parameters that characterize a stimulus waveform 250. Stimulus waveform 250 is the volume flow rate of one or more chemical stimuli that stimulate tissue when delivered in the vicinity of the tissue as a function of time T. The chemical stimuli can be delivered by one or more drug delivery elements (including, e.g., micro- and nano-pumps, syringes, membranes) in implanted portion 105.

In the illustrated implementation, stimulus waveform 250 is characterized by bolus maximum flow rate parameters 255, 260, bolus duration parameters 265, 270, a delay parameter 275, a period parameter 280, and duration parameters 285, 290.

Bolus maximum flow rate parameter 255 characterizes the maximum volume flow rate of a first collection of boluses 292. Bolus maximum flow rate parameter 260 characterizes the maximum volume flow rate of a second collection of boluses 294. Bolus flow rate parameters 255, 260 are generally given in units of volume per time. The maximum flow rate identified by bolus flow rate parameters 255, 260 need not be transitory (as illustrated). Instead, the maximum flow rate can be a steady state flow rate.

Bolus duration parameter 265 characterizes the duration of flow during boluses 292. Bolus duration parameter 270 characterizes the duration of flow during boluses 294. Bolus duration parameters 265, 270 are generally given in units of time.

Delay parameter 275 characterizes the delay between the end of each bolus 292, 294 and the start of the successive bolus 292, 294. Delay parameter 275 is generally given in units of time. As illustrated, delay parameter 275 is constant for all boluses 292, 294. However, this need not be the case. For example, the delay between the end of a bolus 292 and the start of the successive bolus 292 can be longer than the delay between the end of each bolus 294 and the start of the successive bolus 294.

Period parameter 280 characterizes the time between repetitions of identical portions of stimulus waveform 250. Period parameter 280 is generally given in units of time. As illustrated, period parameter 280 characterizes the time between successive onsets of collections of boluses 294. This time can correspond to a diurnal or other repetitive variation in the volume flow rate of one or more chemical stimuli.

Duration parameter 285 characterizes the duration of a collection of boluses 294. Duration parameter 290 characterizes the duration of a collection of boluses 292. Duration parameters 285, 290 are generally given in units of time.

Other stimulation parameters that characterize other classes of stimuli are possible. For example, when tissue is stimulated using electromagnetic radiation, stimulation parameters can characterize the intensity, wavelength, and timing of the electromagnetic radiation stimuli. When tissue is stimulated using mechanical stimuli, stimulation parameters can characterize the pressure, displacement, frequency, and timing of the mechanical stimuli.

Stimulation parameters can also characterize operational characteristics of a stimulation device. Such operational characteristics include which stimulus delivery element is to deliver a stimulus (when multiple elements are available) or which power supply is to power the stimulus (when multiple supplies are available).

Figure 3:
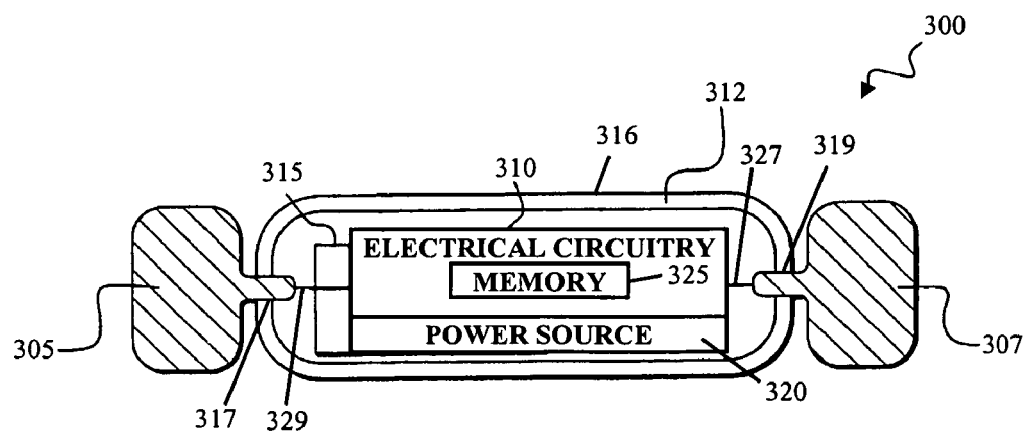
FIG. 3 shows one implementation of an implanted portion of the system of FIG. 1.

FIG. 3 shows one implementation of implanted portion 105, namely a stimulator 300. Stimulator 300 can include a pair of electrodes 305, 307 mounted on a narrow, elongate capsule 312. The outer surface 316 of capsule 312 can be made of a biocompatible material such as biocompatible polymers, glasses, metals, and/or ceramics. Capsule 312 can be sealed to exclude water but permit passage of electromagnetic fields used to transmit data and/or power.

Capsule 312 can have a diameter of less than about 4-5 mm, and less than about 3.5 mm, and less than about 2.5 mm. Capsule 312 can have a length of less than about 30-40 mm, less than about 20-30 mm, and less than about 20 mm. The shape of the capsule 312 can be tailored to the desired target, the surrounding area, and the method of surgical insertion.

Shapes other than the thin, elongated cylinder with electrodes at the ends as shown in FIG. 3, such as disks or helical structures, are possible.

Each electrode 305, 307 traverses the wall of capsule 312 at a respective of openings 317, 319. Electrode 305 can be a stimulating electrode that electrically stimulates tissue, and electrode 307 can be an indifferent electrode that completes the electrical circuit for the stimulating waveform. Electrodes 305, 307 can be made of any biocompatible and conductive material such as conductive ceramics, conductive polymers, and noble or refractory metals (such as gold, silver, platinum, iridium, tantalum, titanium, niobium or their alloys that minimize corrosion, electrolysis, and damage the surrounding tissues).

Capsule 312 houses electronic circuitry 310, a data transceiver 315, and a power source 320. Electronic circuitry 310 can act as a controller that controls and performs operations in stimulator 300, including the receipt of data and/or power, the decoding and storing data, and the generation of electrical stimulation pulses. Electronic circuitry 310 can include a data processing device and/or hardware such as logic circuits, ASIC's, FPGA's, and other devices to control and perform operations in stimulator 300. These operations can include all or portions of the processes described below.

Electronic circuitry 310 includes a memory 325 and is connected to electrodes 305, 307 by electrical leads 327, 329. Memory 325 is a storage device that can store instructions and/or data for controlling the stimulation of tissue. For example, memory 325 can store stimulation parameter information. Electrical leads 327, 329 can be short, flexible leads. For example, leads can be shorter than about 100-150 mm.

Data transceiver 315 includes a transmitter and a receiver and can transmit and receive data from outside of stimulator 300. For example, transceiver 315 can communicate over data link 140 with data transceiver 120 in external portion 110 (FIG. 1).

Power source 320 can supply and store electrical energy for use by stimulator 300. Power source 320 can include a power storage device such as battery or capacitor. Power source 320 can also include a power receiver portion that receives power from outside of stimulator 300, such as an RF link. For example, power source 320 can receive power transmitted over power link 145 from power transmitted 125 in external portion 110 (FIG. 1).

In one implementation of stimulator 300, stimulator 300 is able to generate:
anodic stimulation pulses and cathodic secondary pulses;
a maximum cathodic current of 30 mA, a maximum cathodic current of 8 mA, or a maximum cathodic current of 3 mA;
a maximum cathodic compliance voltage of 30 V, a maximum cathodic compliance voltage of 12 V, or a maximal cathodic compliance voltage of 3 V;
a maximum anodic current of 10 mA, a maximum anodic current of 5 mA, or a maximum anodic current of 0.5 mA;
a maximum anodic compliance voltage of 10 V, a maximum anodic compliance voltage of 5 V, or a maximal anodic compliance voltage of 1 V;
cathodic and anodic pulse widths of between 0.05 and 10.0 msec, pulse widths of between 0.05 and 2.0 msec, or pulse widths of between 0.1 and 0.5 msec; and
a stimulation frequency of between 1 and 200 pulses/second, or a stimulation frequency of between 5 and 50 pulses/second.

In other implementations, stimulator 300 can generate cathodic stimulation pulses and anodic secondary pulses with corresponding characteristics.

Other configurations of stimulator 300 are possible. For example, stimulator 300 can deliver other stimuli such as one or more chemical stimuli, thermal stimuli, electromagnetic stimuli, and/or mechanical stimuli. Stimulator 300 can thus include other stimulus delivery elements.

In one implementation, stimulator 300 can be a BION® microstimulator (Advanced Bionics® Corporation, Valencia, Calif.). Various details associated with the manufacture, operation, and use of BION implantable microstimulators are described in U.S. Pat. Nos. 5,193,539, 5,193,540, 5,312,439, 6,185,452, 6,164,284, 6,208,894, and 6,051,017, the contents of all of which are incorporated herein by reference.

In other implementations, stimulator 300 can include an implantable pulse generator (IPG) coupled to a lead of electrodes, a spinal cord stimulator (SCS), a cochlear implant, a deep brain stimulator, a drug pump, a micro-drug pump, or any other type of implantable stimulator configured to deliver electrical and/or drug stimuli. Example IPG's include those described in U.S. Pat. Nos. 6,381,496, 6,553,263, and 6,760, 626, the contents of all of which are incorporated herein by reference.

Example spinal cord stimulators include those described in U.S. Pat. Nos. 5,501,703, 6,487,446, and 6,516,227, the contents of all of which are incorporated herein by reference. Example cochlear implants include those described in U.S. Pat. Nos. 6,219,580, 6,272,382, and 6,308,101, the contents of all of which are incorporated herein by reference. Example deep brain stimulators include those described in U.S. Pat. Nos. 5,938,688, 6,016,449, and 6,539,263, the contents of all of which are incorporated herein by reference. Example drug pumps include those described in U.S. Pat. Nos. 4,562,751, 4,678,408, 4,685,903, 5,080,653, 5,097,122, 6,740,072, and 6,770,067, the contents of all of which are incorporated herein by reference. Example micro-drug pumps include those described in U.S. Pat. Nos. 5,234,692, 5,234,693, 5,728,396, 6,368,315, 6,666,845, and 6,620,151, the contents of all of which are incorporated herein by reference.

Figure 4A:
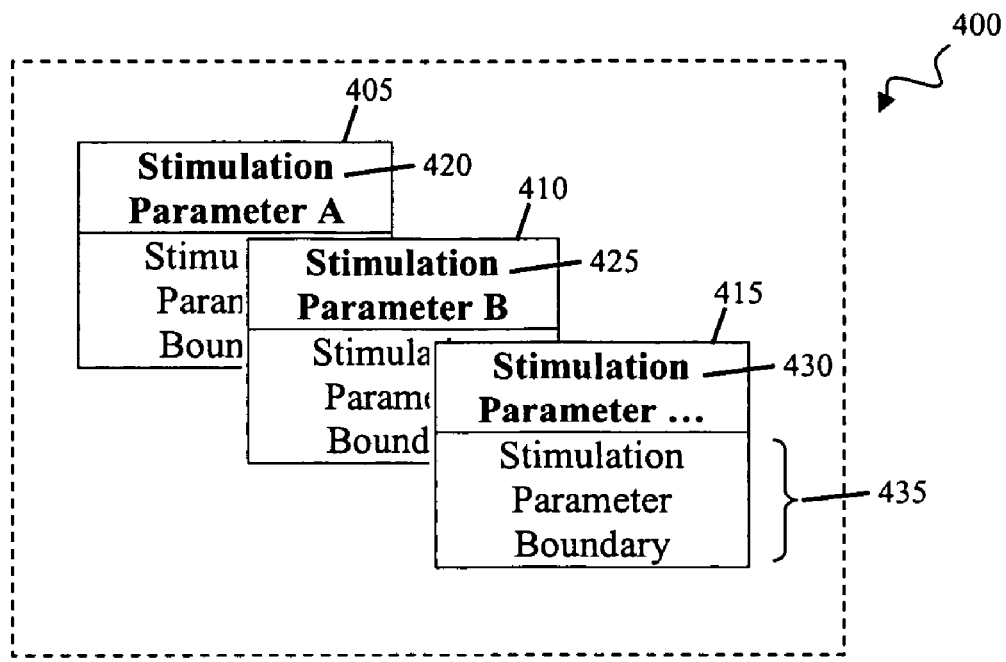
FIG. 4A shows example stimulation parameter information that can be stored in an external portion of a system for stimulating tissue.

FIG. 4A shows example stimulation parameter information 400 that can be stored in an external portion of a system for stimulating tissue. For example, information 400 can be stored in memory 135 of external portion 110 of system 100 (FIG. 1). For the sake of convenience, stimulation parameter information is shown as a collection of data tables 405, 410, 415 that are each assigned to a respective stimulation parameter 420, 425, 430. Each data table 405, 410, 415 includes data 435 representing a stimulation parameter boundary.

Stimulation parameter boundary data 435 identifies boundary values of a stimulation parameter. The boundary values can be the allowable value(s) of a stimulation parameter (e.g., a minimum or a maximum value of a stimulation parameter) or the boundary values can be intermediate values associated with transitions between allowable and disallowed values of a stimulation parameter. Stimulation parameter boundary data 435 can reflect the technical characteristics of implanted portion 105, the nature of the deployment of implanted portion 105, and/or a limit set by medical personnel or a device designer to tailor the stimuli provided by implanted portion 105 to certain ends.

Parameter boundary data 435 can identify the boundary values in a number of different ways. For example, a parameter boundary data 435 can be a particular value (e.g., "15"), a reference to another value (e.g., "15 more than a reference value"), and/or a reference to a memory location or other discrete value (e.g., "the third element in the list [5, 10, 15, 20]"). Parameter boundary data 435 can identify the values themselves (e.g., "the maximum value is 5.0") or using comparisons (e.g., "the maximum value must be less than 5.0").

Stimulation parameter boundary data 435 can include one or more values. For example, stimulation parameter boundary data 435 can include the maximum allowable value of the stimulation pulse amplitude. Alternatively, stimulation parameter boundary data 435 can identify one or more values indirectly using a value, an index, a memory location, or an equation that can be used to identify the values. For example, stimulation parameter boundary data 435 can identify the value of a pulse amplitude boundary using an integer that identifies a pulse amplitude boundary found in a look up table or a by multiplying the integer by a discrete increment or decrement.

Figure 4B:
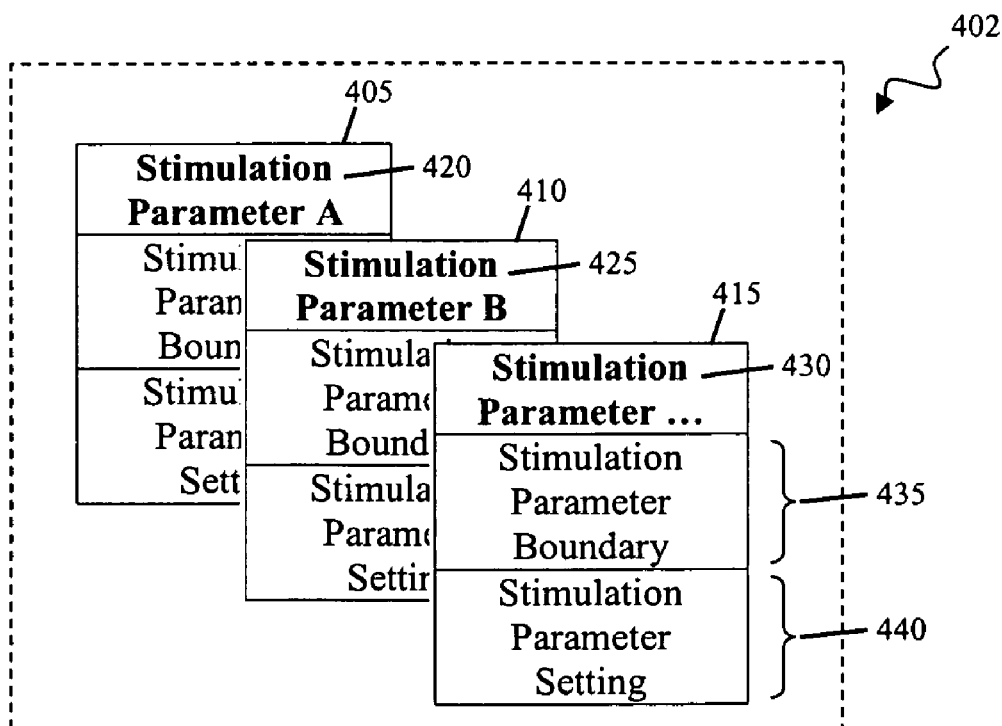
FIG. 4B shows example stimulation parameter information that can be stored in an implanted portion of a system for stimulating tissue.

FIG. 4B shows example stimulation parameter information 402 that can be stored in an implanted portion of a system for stimulating tissue. For example, information 402 can be stored in memory 325 of stimulator 300 (FIG. 3). Once again, stimulation parameter information is shown as a collection of data tables 405, 410, 415 that are each assigned to a respective stimulation parameter 420, 425, 430. In addition to data 435 representing a stimulation parameter boundary, each data table 405, 410, 415 also includes data 440 representing a stimulation parameter setting.

Stimulation parameter setting data 440 identifies the setting of a stimulation parameter that characterizes a stimulus that can be delivered to stimulate tissue. The setting can be the current operational status of the stimulation parameter (e.g., the stimulation pulse amplitude is currently 10 mA) or the setting can be the operational status of the stimulation parameter at some time in the future (e.g., the stimulation pulse amplitude will be 10 mA after a triggering event has occurred).

Stimulation parameter setting data 440 can include one or more setting values. For example, stimulation parameter setting data 440 can include the value of the stimulation pulse amplitude. Alternatively, stimulation parameter setting data 440 can identify one or more settings indirectly using a value, an index, a memory location, or an equation that can be used to identify one or more values. For example, stimulation parameter setting data 440 can identify the setting of a pulse amplitude using an integer that identifies a pulse amplitude found in a look up table or a by multiplying the integer by a discrete increment or decrement.

Other compilations of stimulation parameter information 400, 402 (including hardwired data storage, ROM data storage, data objects, records, files, and lists) that are arranged differently are possible. Further, stimulation parameter information 400, 402 can be stored in a number of different representations in the same system.

FIGS. 5-9 each show different representations of stimulation parameter boundary data 435 in stimulation parameter information 400, 402. As illustrated, every representation identifies both a highest allowable value and a lowest allowable value. However, this need not be the case. For example, a stimulation parameter may only have a highest allowable value, or a stimulation parameter may only have a lowest allowable value. In these cases, only one boundary value need be identified. Further, there may be intermediate boundaries on a stimulation parameter. In these cases, additional boundary values can be identified.

Also, many representations identify ranges of values. The identified ranges of values can be continuous (i.e., all values within the range are possible and/or allowed) or discrete (i.e., only selected values within the range are possible and/or allowed). Discrete values can be identified using, e.g., lists of discrete values, additional table entries, records, or other data objects that identify the selected, discrete values.

Figure 5:
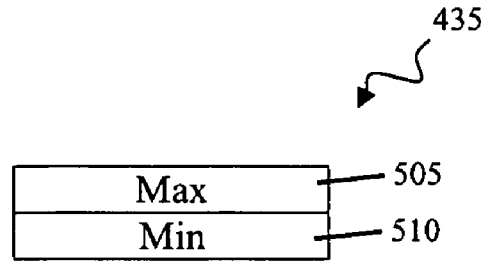
FIGS. 5-9 each shows different representations of stimulation parameter boundary data.

In FIG. 5, stimulation parameter boundary data 435 includes a maximum value field 505 and a minimum value field 510. Maximum value field 505 identifies the highest allowable value of a stimulation parameter, whereas minimum value field 510 identifies the lowest allowable value of the stimulation parameter.

Figure 6:
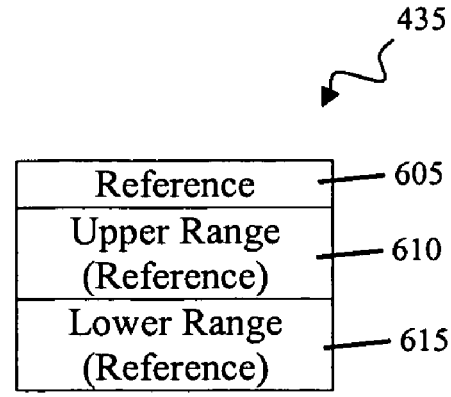

In FIG. 6, stimulation parameter boundary data 435 includes a reference value field 605, an upper range (relative to the reference) field 610, and a lower range (relative to the reference) field 615. Reference value field 605 identifies a reference value of a stimulation parameter. A reference value is a particular value of a stimulation parameter. Example reference values include a period of two seconds, a pulse amplitude of five millivolts, and a duration of one minute.

Upper range field 610 identifies a range of allowable values above the reference value of the stimulation parameter. Lower range field 615 identifies a range of allowable values below the reference value of the stimulation parameter.

Figure 7:
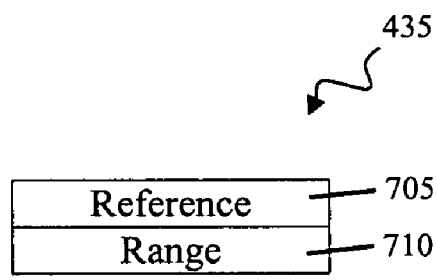

In FIG. 7, stimulation parameter boundary data 435 includes a reference value field 705 and a range field 710. Reference value field 705 identifies a reference value of the allowable range of stimulation parameters.

In one implementation, range field 710 identifies a range of allowable values above the reference value and a range of allowable values below the reference value. Thus, the upper boundary is above the reference value identified in reference value field 705 by the range identified in range field 710. The lower boundary is below the reference value identified in reference value field 705 by the range identified in range field 710. The total range of allowable values is twice the range identified in range field 710.

In another implementation, range field 710 identifies a range of allowable values that is centered on the reference value. Thus, the upper boundary is above the reference value identified in reference value field 705 by one half of the range identified in range field 710. The lower boundary is below the reference value identified in reference value field 705 by one half of the range identified in range field 710. The total range of allowable values is equal to the range identified in range field 710.

In another implementation, range field 710 identifies the range of allowable stimulation parameters below the reference value. Thus, the upper boundary is the reference value identified in reference value field 705. The lower boundary is below the reference value identified in reference value field 705 by the range identified in range field 710.

In another implementation, range field 710 identifies the range of allowable stimulation parameters above the reference value. Thus, the lower boundary is the reference value identified in reference value field 705. The upper boundary is above the reference value identified in reference value field 705 by the range identified in range field 710.

Figure 8:
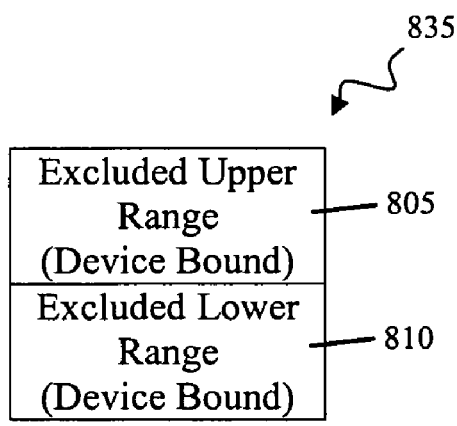

In FIG. 8, stimulation parameter boundary data 435 includes an excluded upper range field 805 and an excluded lower range field 810. Excluded range fields 805, 810 identify ranges of unallowable or impossible values. In particular, excluded upper range field 805 identifies the range of values below an upper, device-specific boundary from which a parameter setting is excluded. For example, if the device-specific maximum value of a stimulation pulse current amplitude is 30 mA, excluded upper range field 805 can identify a range of 10 mA below this device-specific value from which the pulse current amplitude parameter setting is excluded. The resultant, operational maximum value of the current amplitude parameter setting would then be 20 mA.

Excluded lower range field 810 identifies the range of values above a lower, device-specific boundary from which the current parameter setting is excluded. For example, if the device-specific minimum value of a stimulation pulse current amplitude is 0.01 mA, excluded lower range field 810 can identify a range of 0.49 mA above this device-specific value from which the pulse current amplitude parameter setting is excluded. The resultant, operational minimum value of the current amplitude parameter setting would then be 0.5 mA.

Figure 9:
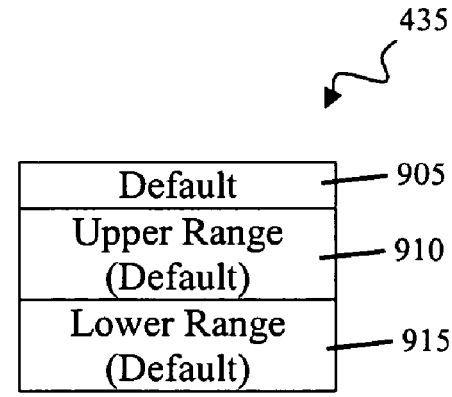

In FIG. 9, stimulation parameter boundary data 435 includes a default value field 905, an upper range (relative to the default) field 910, and a lower range (relative to the default) field 915. Default value field 905 identifies the default value of a stimulation parameter. Upper range field 910 identifies the range of allowable values above the default value of the stimulation parameter. Lower range field 915 identifies the range of allowable values below the default value of the stimulation parameter.

Figure 10:
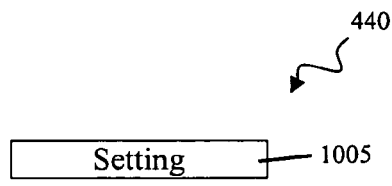
FIGS. 10-13 each shows different representations of stimulation parameter setting data.

FIGS. 10-13 each show different representations of stimulation parameter setting data 440 in stimulation parameter information 402. In FIG. 10, stimulation parameter setting data 440 includes a setting field 1005. Setting field 1005 directly identifies the value of the setting of a stimulation parameter.

Figure 11:
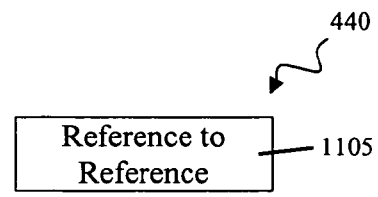

In FIG. 11, stimulation parameter setting data 440 includes a field referenced to a reference value 1105. Field 1105 identifies the value of the setting of a stimulation parameter relative to the reference value. The reference value can be identified, e.g., by fields 605, 705 in stimulation parameter boundary data 435 and can be an extreme boundary value, a default value, an average value, and intermediate boundary, and the like.

Figure 12:
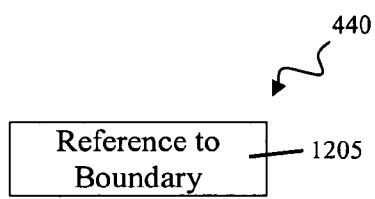

In FIG. 12, stimulation parameter setting data 440 includes a field referenced to a boundary value 1205. Field 1205 identifies the value of the setting of a stimulation parameter relative to a boundary value. The boundary value can be identified, e.g., by one or more of fields 605, 610, 615, 705, 710, 805, 810, 905, 910, 915 in stimulation parameter boundary data 435.

Figure 13:
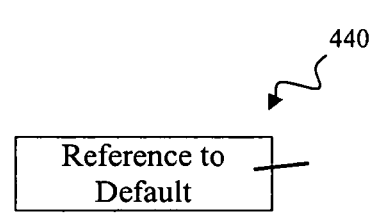

In FIG. 13, stimulation parameter setting data 440 includes a field referenced to a default value 1305. Field 1305 identifies the value of the setting of a stimulation parameter relative to a default value. The default value can be identified, e.g., by field 905 in stimulation parameter boundary data 435.

Figure 14:
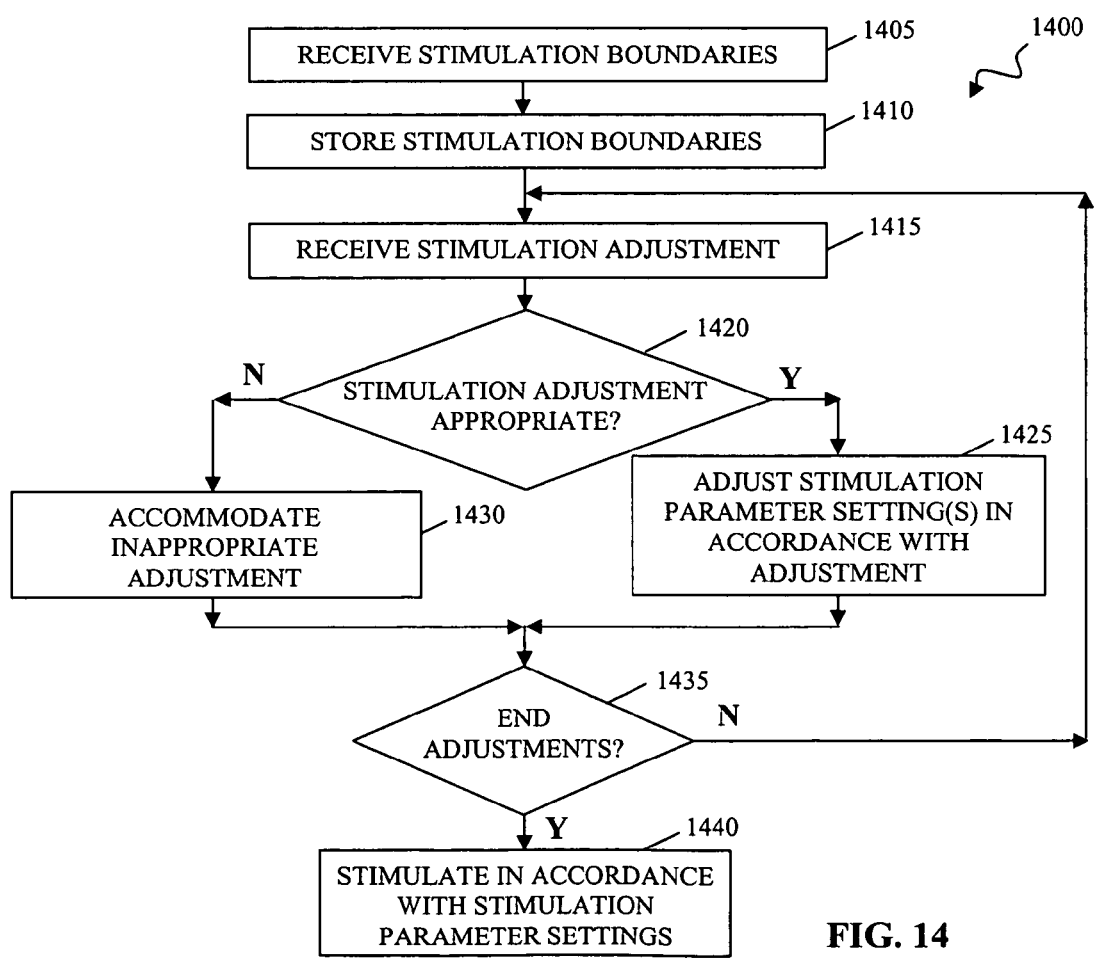
FIG. 14 shows a process for controlling the stimulation of tissue.

FIG. 14 shows a process 1400 for controlling the stimulation of tissue. Process 1400 can be performed by a system for stimulating tissue such as system 100.

The system performing process 1400 can receive stimulation boundaries at 1405. The received stimulation boundaries can identify the allowable value of a stimulation parameter. The stimulation boundaries can be received from a user such as a medical professional who is tailoring the range of stimuli that can be provided by implanted portion 105 to a specific medical application. The stimulation boundaries can be received over a user interface such as user interface 115 (FIG. 1).

The system can also store the received stimulation boundaries at 1410. The stimulation boundaries can identify allowable value(s) of one or more stimulation parameters, such as parameters 215, 220, 225, 230, 235, 240, 245, 255, 260, 265, 270, 275, 280, 285, 290 (FIGS. 2A, 2B). The stimulation boundaries 435 can be stored in collection 400 (FIG. 4A) in memory 135 in external portion 110 of system 100 (FIG. 1). The stimulation boundaries 435 can also be stored in collection 402 (FIG. 4B) in memory 325 in stimulator 300 (FIG. 3). The stored stimulation boundaries 435 can be represented as shown in one or more of FIGS. 5-9.

The system can also receive one or more stimulation adjustments at 1415. Stimulation adjustments are proposed changes to the stimulation parameter settings. The proposed changes can include a complete new value of a parameter setting and/or changes relative to one or more existing parameter settings (including a default setting). For example, a proposed change can be a proposal to increase an existing parameter setting by an incremental amount (or decrease an existing parameter setting by an decremental amount) that is identified in memory 135 of external portion 110 (FIG. 1) or in memory 325 of stimulator 300 (FIG. 3). As another example, a proposed change can be a proposal to increase an existing parameter setting by an incremental amount (or decrease an existing parameter setting by an decremental amount) that is calculated by processor 130 of external portion 110 based on the contents of memory 135 (FIG. 1) or the contents of memory 325 of stimulator 300 (FIG. 3). As yet another example, a proposed change can be the incremental amount by which one or more one or more existing parameter settings are to be increased (or a decremental amount by which one or more one or more existing parameter settings are to be decreased).

The proposed change(s) can impact one or more stimulation parameters, such as parameters 215, 220, 225, 230, 235, 240, 245, 255, 260, 265, 270, 275, 280, 285, 290 (FIGS. 2A, 2B). The stimulation adjustments can be received over a user interface such as user interface 115 (FIG. 1).

The system can determine if the proposed stimulation adjustment is appropriate at 1420. Determining if the proposed adjustment is appropriate can include comparing the proposed adjustment to one or more stored stimulation boundaries to ensure that the proposed adjustment is within the stimulation boundaries. The determination of whether or not a proposed stimulation adjustment is appropriate is described further below.

If the system determines that the proposed stimulation adjustment is appropriate, then the system can adjust one or more stimulation parameter settings in accordance with any appropriate stimulation adjustment at 1425. This adjustment can include changing a stimulation parameter setting to a value proposed by the stimulation adjustment. For example, a stimulation parameter setting 440 that is stored in collection 402 (FIG. 4B) in memory 325 in stimulator 300 (FIG. 3) can be changed. The changed stimulation parameter setting 440 can be represented as shown in one or more of FIGS. 10-13.

On the other hand, if the system determines that the proposed stimulation adjustment is inappropriate, the system can accommodate the inappropriate adjustment at 1430. This accommodation is also discussed in further detail below.

With a stimulation parameter setting adjusted or an inappropriate adjustment accommodated, the system can determine if adjustments are to end at 1435. This determination can be made based on a number of different factors including the existence of unset stimulation parameters, user input indicating that adjustments are to end, or a lack of user input over time.

If the system determines that adjustments are indeed to end, then the system can stimulate in accordance with the existing stimulation parameter settings at 1440. However, if adjustments are not going to end, then the system can receive additional proposed stimulation adjustment(s) at 1415.

Figure 15:
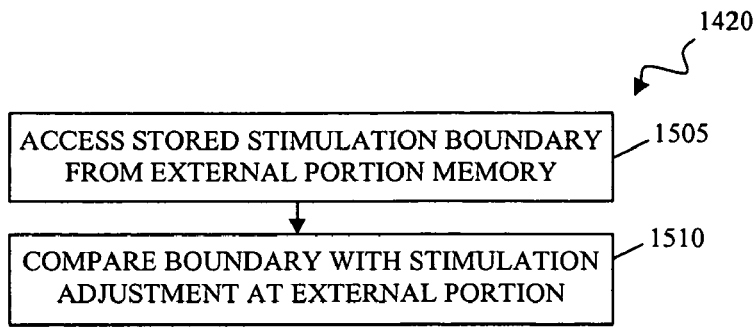
FIGS. 15-17 show examples of processes for determining if a stimulation adjustment is appropriate.
Figure 16:
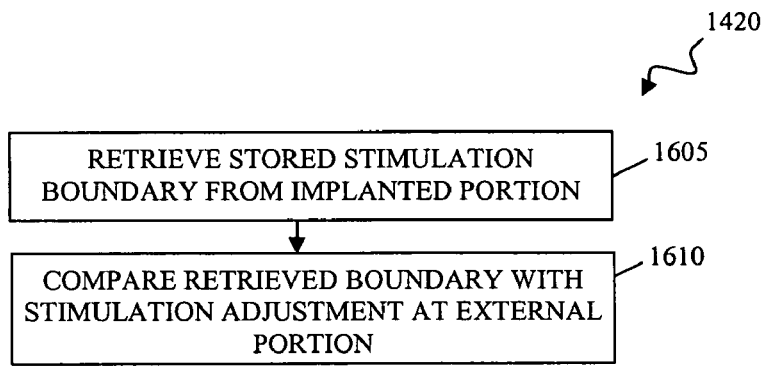
Figure 17:
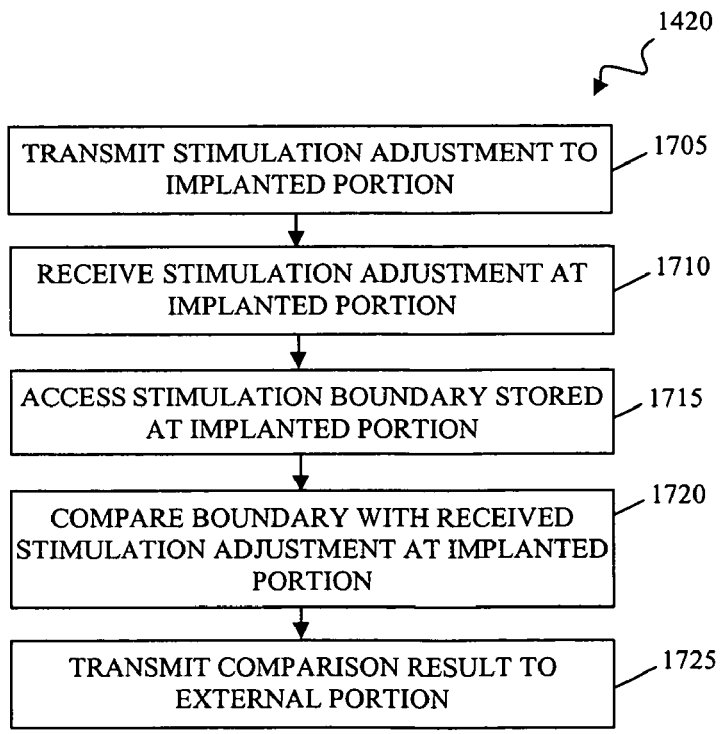

FIGS. 15-17 show examples of processes for determining if a stimulation adjustment is appropriate at 1420 in process 1400 (FIG. 14).

As shown in FIG. 15, in determining if a stimulation adjustment is appropriate, the system performing process 1400 can access a stored stimulation boundary from a memory of external portion of a system for stimulating tissue at 1505. If process 1400 is performed by a system such as system 100

(FIG. 1), processor 130 can access a stored stimulation boundary in memory 135 over a memory controller or other interface device. For example, processor 130 can read stimulation parameter boundary data 435 from a collection 400 (FIG. 4A).

The system can compare a stimulation boundary with a proposed stimulation adjustment to determine if the stimulation adjustment is appropriate at 1510. The comparison can include determining if the proposed stimulation adjustment would bring the stimulation parameter setting outside a range of allowed or possible stimulation parameter values defined by the stimulation boundary. Depending on the representation of stimulation parameter boundary data 435 in collection 400, processor 130 can process stimulation parameter boundary data 435 or a proposed stimulation adjustment so that a meaningful comparison can be made.

As shown in FIG. 16, in determining if a stimulation adjustment is appropriate, the system performing process 1400 can also retrieve a stored stimulation boundary from a memory in an implanted portion of a device for stimulating tissue at 1605. If process 1400 is performed by a system such as system 100 (FIG. 1), processor 130 can direct data transceiver 120 to instruct implanted portion 105 to return a stimulation boundary stored at implanted portion 105 to transceiver 120. For example, the stimulation boundary stored at implanted portion 105 can be stimulation parameter boundary data 435 from a collection 402 (FIG. 4B) that is stored at a memory 325 in a stimulator 300 (FIG. 3).

At the external portion, the system can compare the retrieved stimulation boundary with a proposed stimulation adjustment to determine if the stimulation adjustment is appropriate at 1610. The comparison can include determining if the proposed stimulation adjustment would bring the stimulation parameter setting outside a range of allowed or possible stimulation parameter values defined by the stimulation boundary. If process 1400 is performed by a system such as system 100 (FIG. 1), processor 130 can perform the comparison. Depending on the representation of stimulation parameter boundary data 435 retrieved from implanted portion 105, processor 130 can process stimulation parameter boundary data 435 or a proposed stimulation adjustment so that a meaningful comparison can be made.

As shown in FIG. 17, in determining if a stimulation adjustment is appropriate, the system performing process 1400 can also transmit the proposed stimulation adjustment to an implanted portion of a device for stimulating tissue at 1705. If process 1400 is performed by a system such as system 100 (FIG. 1), processor 130 can direct data transceiver 120 to transmit the proposed stimulation adjustment to implanted portion 105 over data link 140.

The implanted portion of the system performing process 1400 can receive the proposed stimulation adjustment at 1710. For example, an implanted portion such as stimulator 300 can receive the stimulation adjustment over data transceiver 315 (FIG. 3).

The implanted portion can access a locally stored stimulation boundary at 1715. For example, electrical circuitry 310 (FIG. 3) can access stimulation parameter boundary data 435 from a collection 402 (FIG. 4B) that is stored at a memory 325 in a stimulator 300 (FIG. 3).

At the implanted portion, the system can compare the stimulation boundary with the received proposed stimulation adjustment to determine if the stimulation adjustment is appropriate at 1720. The comparison can include determining if the proposed stimulation adjustment would bring the stimulation parameter setting outside a range of allowed or possible stimulation parameter values defined by the stimulation boundary. If process 1400 is performed by a system that includes an implanted stimulator 300 (FIG. 3), electrical circuitry 310 can perform the comparison. Depending on the representation of stimulation parameter boundary data 435 in collection 402, electrical circuitry 310 can process stimulation parameter boundary data 435 or a proposed stimulation adjustment so that a meaningful comparison can be made.

The implanted portion can also transmit a result of the comparison to the external portion at 1725. The transmitted result can be used for further interaction with a user, as discussed further below.

Figure 18:
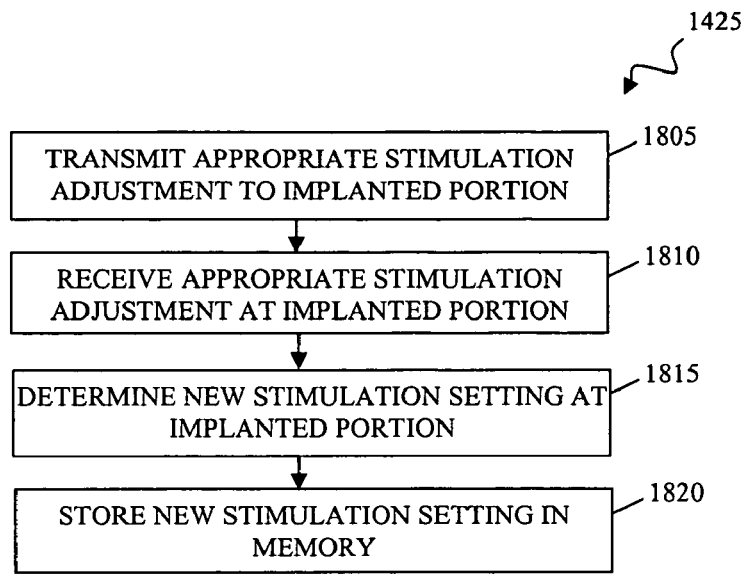
FIGS. 18-20 show examples of processes for adjusting one or more stimulation parameter settings in accordance with an appropriate stimulation adjustment.
Figure 19:
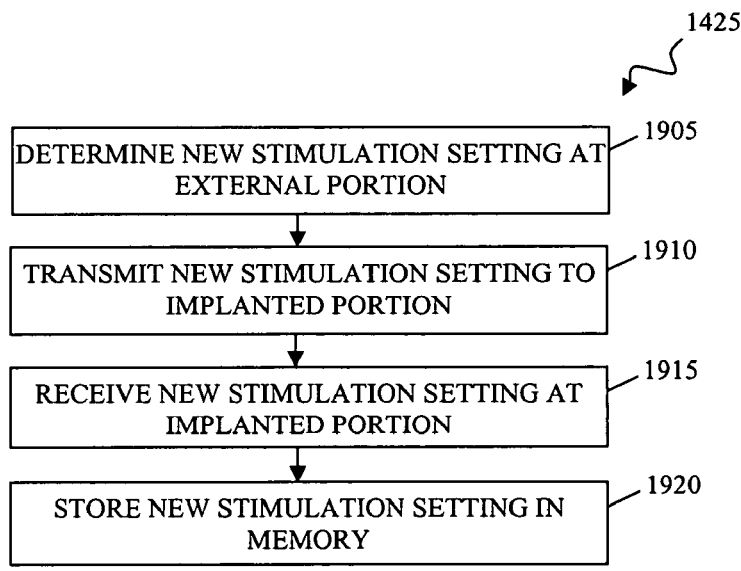
Figure 20:
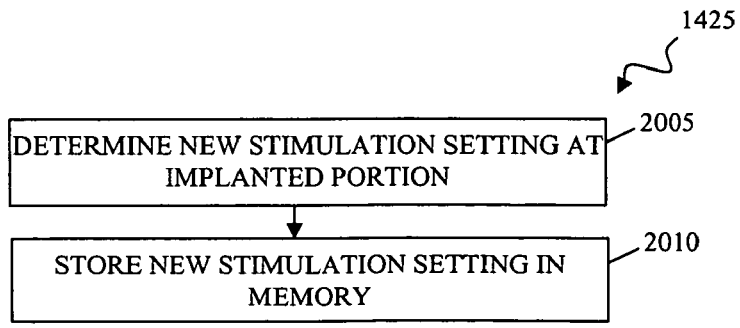

FIGS. 18-20 show examples of processes for adjusting one or more stimulation parameter settings in accordance with an appropriate stimulation adjustment at 1425 in process 1400 (FIG. 14).

As shown in FIG. 18, in adjusting one or more stimulation parameter settings in accordance with appropriate stimulation adjustment, the system performing process 1400 can transmit the appropriate adjustment to an implanted portion at 1805. This assumes that a determination as to whether or not a stimulation adjustment is appropriate has been performed at an external portion. If process 1400 is performed by a system such as system 100 (FIG. 1), processor 130 can direct data transceiver 120 to transmit the appropriate stimulation adjustment to implanted portion 105 over data link 140.

The system performing process 1400 can receive the appropriate stimulation adjustment at an implanted portion at 1810. If the system performing process 1400 includes a stimulator 300, transceiver 315 can receive the stimulation adjustment (FIG. 3).

The system can also determine a new stimulation setting at the implanted portion at 1815. The determination of a new setting can depend on the nature of the stimulation adjustment. For example, if the stimulation adjustment is a complete new value of a parameter setting, determining the new setting need only include identifying which parameter is to be set to the new setting. As another example, if the stimulation adjustment is a change relative to a existing parameter setting, determining the new setting can also include computing the new setting based on the existing parameter setting and the appropriate change. As another example, if the stimulation adjustment is a change to an integer that is used to identify the stimulation setting, determining the new setting can also include using the changed integer to look up the new stimulation setting or multiplying the changed integer by a certain increment or decrement. If the system includes a stimulator 300, the new stimulation setting can be determined by electrical circuitry 310 (FIG. 3).

The system can also store the new stimulation setting in a memory at the implanted portion at 1820. This storage can include a write operation to one or more memory devices over a memory interface. If the system includes a stimulator 300, the new stimulation setting can be stored at memory 325 by electrical circuitry 310 (FIG. 3).

As shown in FIG. 19, in adjusting one or more stimulation parameter settings in accordance with appropriate stimulation adjustment, the system performing process 1400 can determine a new stimulation setting at the external portion at 1905. This assumes that a determination as to whether or not a stimulation adjustment is appropriate has been performed at an external portion. The determination of a new setting can depend on the nature of the stimulation adjustment. For example, if the stimulation adjustment is a complete new value of a parameter setting, determining the new setting need only include identifying which parameter is to be set to the new setting. As another example, if the stimulation adjustment is a change relative to a existing parameter setting, determining the new setting can also include computing the new setting based on the existing parameter setting and the appropriate change. As another example, if the stimulation adjustment is a change to an integer that is used to identify the stimulation setting, determining the new setting can also include using the changed integer to look up the new stimulation setting or multiplying the changed integer by a certain increment or decrement. If the system performing process 1400 is system 100, the new stimulation setting can be determined by processor 130 (FIG. 1).

The system can also transmit the appropriate adjustment to an implanted portion at 1910. If process 1400 is performed by a system such as system 100 (FIG. 1), processor 130 can direct data transceiver 120 to transmit the new stimulation setting to implanted portion 105 over data link 140.

The system performing process 1400 can receive the new stimulation setting at an implanted portion at 1915. If the system performing process 1400 includes a stimulator 300, transceiver 315 can receive the new stimulation setting (FIG. 3).

The system can also store the new stimulation setting in a memory at the implanted portion at 1920. This storage can include a write operation to one or more memory devices over a memory interface. If the system includes a stimulator 300, the new stimulation setting can be stored at memory 325 by electrical circuitry 310 (FIG. 3).

If a determination as to whether or not a stimulation adjustment is appropriate has been performed at an internal portion, the internal portion can also determine a new stimulation setting, if needed. As shown in FIG. 20, in adjusting one or more stimulation parameter settings in accordance with appropriate stimulation adjustment, the system performing process 1400 can determine a new stimulation setting at the implanted portion at 2005. The determination of a new setting can depend on the nature of the stimulation adjustment. For example, if the stimulation adjustment is a complete new value of a parameter setting, determining the new setting need only include identifying which parameter is to be set to the new setting. As another example, if the stimulation adjustment is a change relative to a existing parameter setting, determining the new setting can also include computing the new setting based on the existing parameter setting and the appropriate change. As another example, if the stimulation adjustment is a change to an integer that is used to identify the stimulation setting, determining the new setting can also include using the changed integer to look up the new stimulation setting or multiplying the changed integer by a certain increment or decrement. If the system performing process 1400 includes a stimulator 300, the new stimulation setting can be determined by electrical circuitry 310 (FIG. 3).

The system can also store the new stimulation setting in a memory at the implanted portion at 2010. This storage can include a write operation to one or more memory devices over a memory interface. If the system includes a stimulator 300, the new stimulation setting can be stored at memory 325 by electrical circuitry 310 (FIG. 3).

Figure 21:
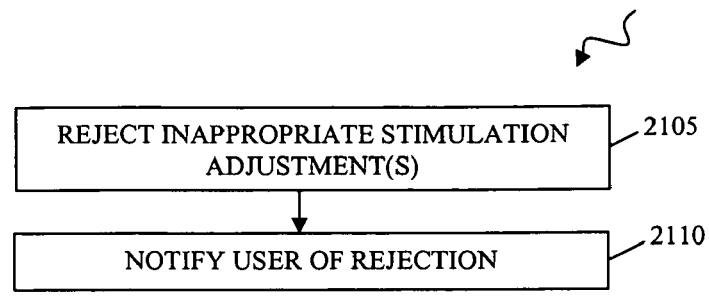
FIGS. 21, 22 show examples of processes for accommodating inappropriate adjustments.
Figure 22:
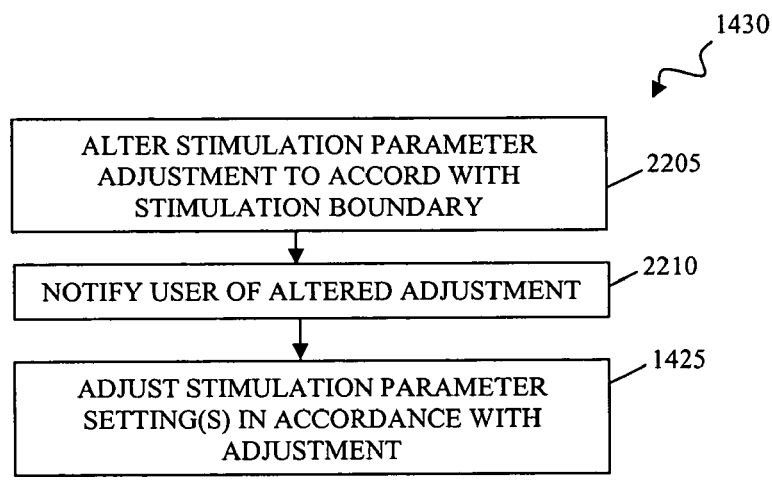

FIGS. 21-22 show examples of processes for accommodating inappropriate adjustments at 1430 in process 1400 (FIG. 14).

As shown in FIG. 21, in accommodating one or more inappropriate adjustments, the system performing process 1400 can reject an inappropriate stimulation adjustment at 2105. The rejection of an inappropriate adjustment results in the current stimulation parameter settings remaining unchanged. The rejection of an inappropriate adjustment can include one or more affirmative acts and/or omissions. Examples of affirmative acts include, e.g., disabling a default procedure for transmitting the adjustment or a setting to an implanted portion or disabling a default procedure for determining a setting based on the adjustment. Examples of omissions include failing to trigger the transmission of an adjustment or setting to an implanted portion or failing to enable a procedure for determining a setting based on the adjustment.

The rejection of an inappropriate adjustment can be made at an implanted portion or an external portion of a system for stimulating tissue. For example, if the determination of whether or not an adjustment is appropriate is made at an implanted portion, the rejection can also be made at the implanted portion. As another example, if the determination of whether or not an adjustment is appropriate is made at an external portion, the rejection can be made at the external portion or at the implanted portion after notice of the inappropriateness of the adjustment has been communicated to the implanted portion.

After the rejection has been made, the system performing process 1400 can notify the user of the rejection at 2110. The notification can be made over one or more output devices. For example, if process 1400 is performed by system 100, user interface 115 in external portion 110 can notify the user of the rejection.

As shown in FIG. 22, in accommodating one or more inappropriate adjustments, the system performing process 1400 can alter a stimulation parameter adjustment to accord with a stimulation boundary at 2205. Such an alteration can including modifying the proposed stimulation parameter adjustment so that a parameter setting that would result from the modified adjustment will be within the stimulation parameter boundary that was violated. For example, suppose that (1) a certain stimulation parameter has a lower boundary of 2.0; and (2) a proposed stimulation adjustment would yield a corresponding stimulation parameter setting with a value of 1.0.

With this proposed adjustment bringing the stimulation parameter setting below the lower boundary of the stimulation parameter (i.e., below the lowest allowable value of the stimulation parameter), the stimulation adjustment is inappropriate. The system performing process 1400 can accommodate this inappropriate adjustment at 2205 by changing the stimulation parameter adjustment to yield a parameter setting of 2.0 rather 1.0.

The alteration of an inappropriate adjustment can be made at an implanted portion or an external portion of a system for stimulating tissue. For example, if the determination of whether or not an adjustment is appropriate is made at an implanted portion, the alteration can also be made at the implanted portion. As another example, if the determination of whether or not an adjustment is appropriate is made at an external portion, the alteration can be made at the external portion or at the implanted portion after notice of the inappropriateness of the adjustment has been communicated to the implanted portion.

After the alteration has been made, the system performing process 1400 can notify the user of the alteration at 2210. The notification can be made over one or more output devices. For example, if process 1400 is performed by system 100, user interface 115 in external portion 110 can notify the user of the alteration.

The system performing process 1400 can also adjust one or more stimulation parameter settings in accordance with the altered stimulation adjustment at 1425. This adjustment can include changing a stimulation parameter setting to a value yielded with the altered stimulation adjustment. The stimulation parameter setting can be adjusted in accordance with any of the processes described in FIGS. 18-20. For example, a stimulation parameter setting 440 that is stored in collection 402 (FIG. 4B) in memory 325 in stimulator 300 (FIG. 3) can be changed. The changed stimulation parameter setting 440 can be represented as shown in one or more of FIGS. 10-13.

Figure 23:
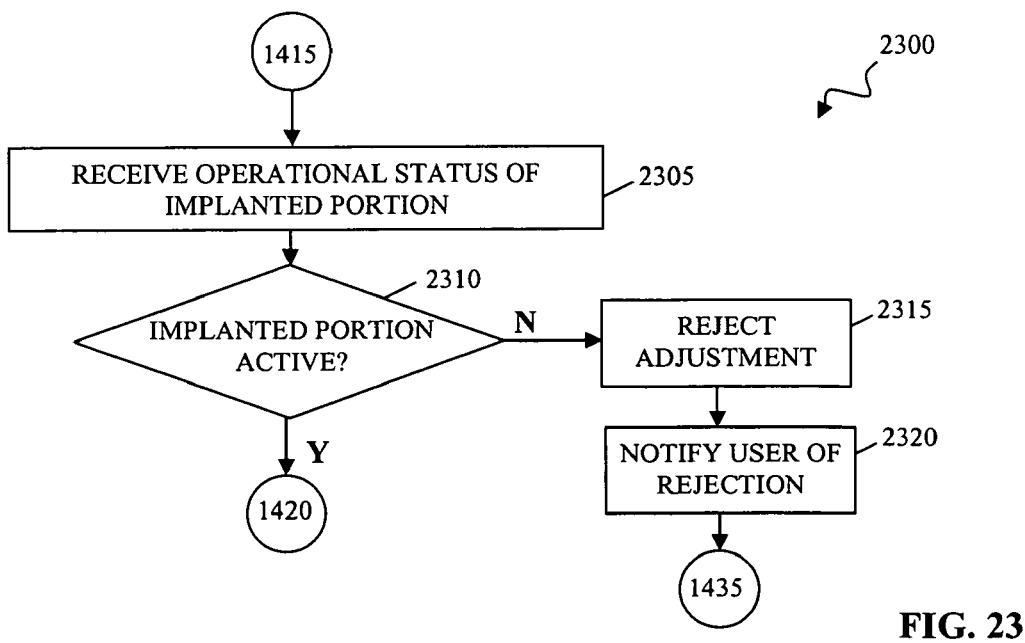
FIGS. 23, 24 show processes for controlling the stimulation of tissue based on the operational status of an implanted portion.

FIG. 23 shows a process 2300 for controlling the stimulation of tissue based on the operational status of an implanted portion. Process 2300 can be performed at an external portion of a system for stimulating tissue, such as external portion 110 of system 100 (FIG. 1).

Process 2300 can be performed as part of another process. For example, the illustrated implementation of process 2300 is shown integrated into process 1400. However, this need not be the case. Instead, process 2300 can be implemented as an independent element, as a component of other processes, or integrated into process 1400 in a different manner.

The system performing process 2300 can receive information regarding the operational status of the implanted portion at 2305. The operational status information can be used to determine whether or not the implanted portion is active. Activity in the implanted portion at 2305 can include the instantaneous delivery of a stimulating pulse, the instantaneous delivery of a secondary pulse, as well as various periods between stimulating pulses and a secondary pulses where charge is not delivered or received.

The operational status information can be received from an implanted portion or from a flag or memory register that is set to indicate the operational status of an implanted portion. For example, if process 2300 is performed by system 100, operational status information can be received over data link 140 from implanted portion 105 or from a flag in memory 135 that is set in accordance with the operational status of implanted portion 105 (FIG. 1).

The system performing process 2300 can determine whether or not the implanted portion is active at 2310. If the implanted portion generates electrical stimuli as shown in waveform 200 (FIG. 2A), the implanted portion is stimulating tissue if it is set to generate a stimulation pulse 205 within a period 240.

If the system determines that the implanted portion is currently stimulating tissue, the system can proceed with normal operation. For example, the system can determine whether or not a proposed stimulation adjustment is appropriate at 1420 (FIG. 14).

If the system determines that the implanted portion is not active, then the system can reject any adjustment at 2315. The rejection results in the current stimulation parameter settings remaining unchanged. The rejection can include one or more affirmative acts and/or omissions.

A user can be notified of the rejection at 2320. The notification can be made over one or more output devices. For example, if process 1400 is performed by system 100, user interface 115 in external portion 110 can notify the user of the rejection.

Figure 24:
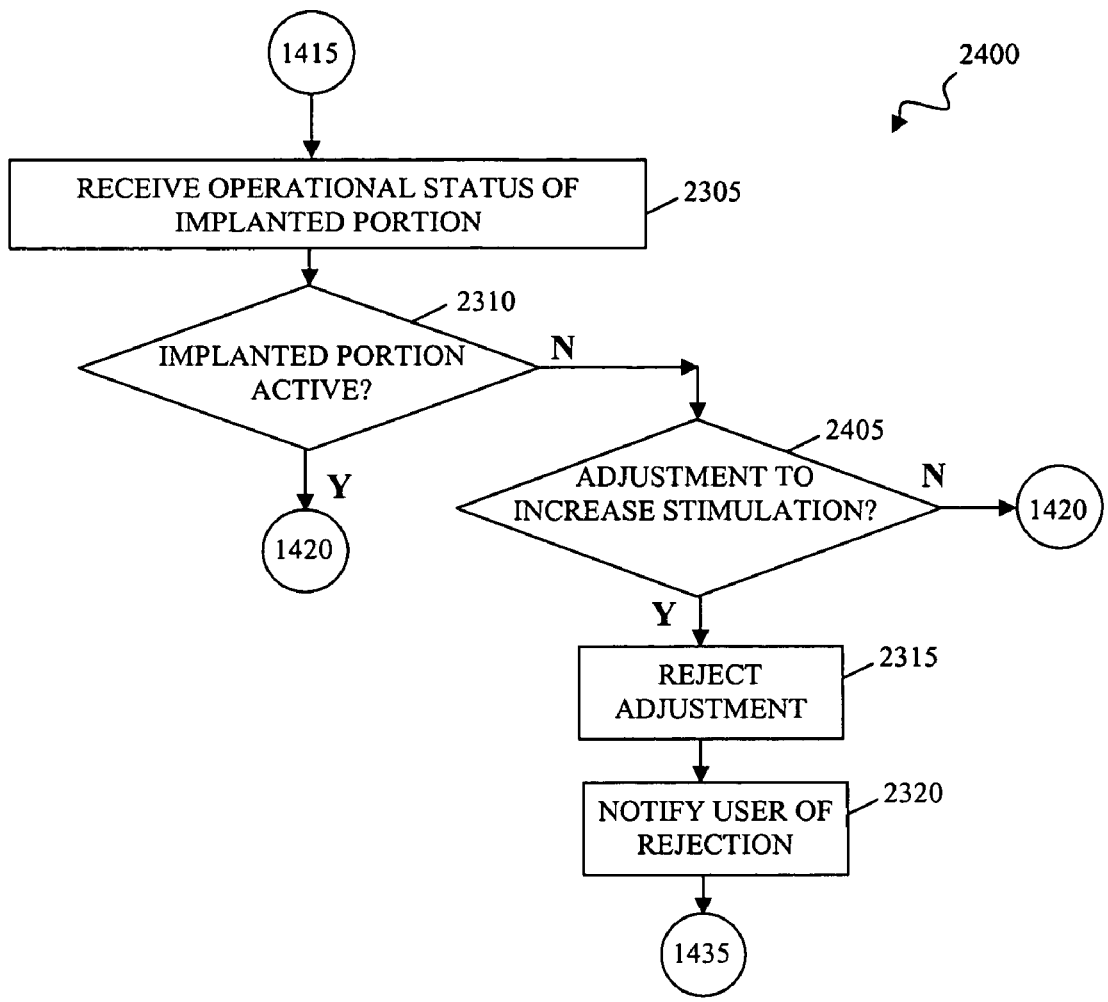

FIG. 24 shows a process 2400 for controlling the stimulation of tissue based on the operational status of an implanted portion. Process 2400 can be performed at an external portion of a system for stimulating tissue, such as external portion 110 of system 100 (FIG. 1).

Process 2400 can be performed as part of another process. For example, the illustrated implementation of process 2400 is shown integrated into process 1400. However, this need not be the case. Instead, process 2400 can be implemented as an independent element, as a component of other processes, or integrated into process 1400 in a different manner.

The system performing process 2400 can receive information regarding the operational status of the implanted portion at 2305. If the system determines that the implanted portion is not currently stimulating tissue at 2310, then the system can determine whether or not the proposed adjustment would increase the stimulation at 2405. Increasing the stimulation involves changing one or more characteristics of stimuli so that the likelihood of tissue being stimulated is increased, the number of times over a certain period that tissue is stimulated is increased, and/or the amount of tissue stimulated is increased. For example, if the implanted portion generates electrical stimuli as shown in waveform 200 (FIG. 2A), the stimulation of tissue may, in certain circumstances, be increased when the primary pulse amplitude (characterized by primary pulse amplitude parameter 215) is increased, when the primary pulse duration (characterized by primary pulse duration parameter 220) is increased, when the waveform period (characterized by period parameter 240) is decreased, and/or when the rising slope of primary pulses (characterized by pulse shape parameter 245) is increased. As another example, if the implanted portion deliver chemical stimuli as shown in waveform 250 (FIG. 2B), the stimulation of tissue may, in certain circumstances, be increased when the maximum flow rate of chemical (characterized by bolus maximum flow rate parameters 255, 260) is increased, when the duration of a chemical bolus (characterized by bolus maximum flow rate parameters 265) is increased, when the delay between boluses (characterized by delay parameter 275) is decreased, or when the period during which boluses 292 (characterized by duration parameters 290) is increased.

If the system determines that the proposed adjustment would increase the stimulation of tissue, then the system can reject the adjustment at 2315 and notify the user of the rejection at 2320. If the system determines that the proposed adjustment would not increase the stimulation of tissue, the system can proceed with normal operation. For example, the system can determine whether or not a proposed stimulation adjustment is appropriate at 1420 (FIG. 14).

In both processes 2300, 2400, changes to the stimulation of tissue while the an implanted portion is not operational are hindered. This can prevent large changes from being implemented while the implanted portion is not operational. This can prevent cell damage and/or necrosis that could result when a user makes large changes in stimulation settings without immediate awareness of the consequences of those changes.

Figure 25:
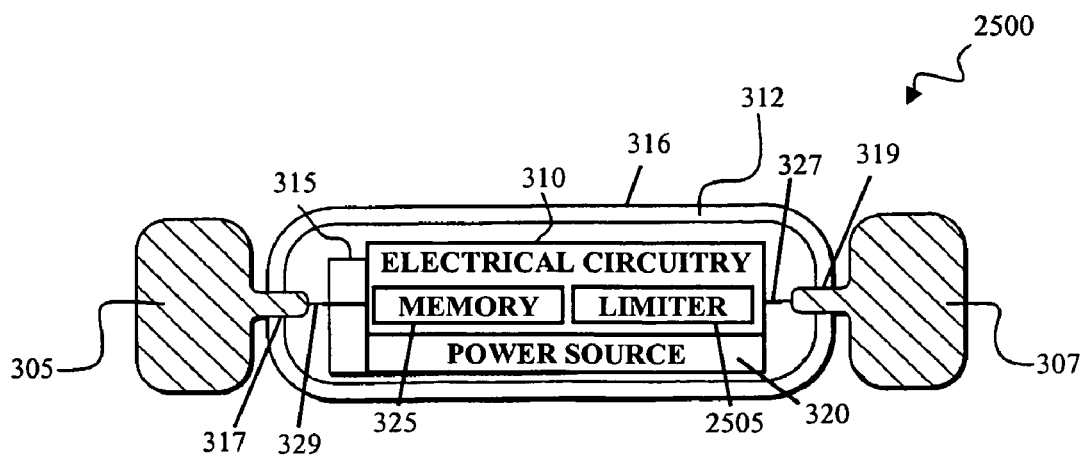
FIG. 25 shows another example of an implanted portion of the system of FIG. 1.

FIG. 25 shows another example of implanted portion 105, namely an electrical stimulator 2500. Stimulator 2500 includes electrodes 305, 307 and capsule 312. In addition to electronic circuitry 310, data transceiver 315, and power source 320, capsule 312 houses a stimulation limiter 2505.

Stimulation limiter 2505 is hardware that defines the allowable values of one or more stimulation parameters independently of other elements of electrical circuitry 310. For example, stimulation limiter 2505 can be a charge, a power, a voltage, and/or a current limiter that ensures that a stimulation pulse will never exceed a certain charge, power, and/or amplitude. As another example, stimulation limiter 2505 can be dosage limiter such as a predefined maximum volume or a flowmeter coupled to a shut-off valve that has been hardwired to limit an amount of drug delivered. Stimulation limiter 2505 can include various hardware elements such as FPGA's, hardwired logic, and/or ASIC's that define the allowable values of one or more stimulation parameters independently of other elements of electrical circuitry 310.

Stimulation limiter 2505 includes tangible components. Thus, stimulation limiter 2505 is not an inherent characteristic of other components of stimulator 2500. For example, limiter 2505 is not a supply voltage of stimulator 2500 that limits the voltage amplitude of a stimulation pulse.

Figure 26:
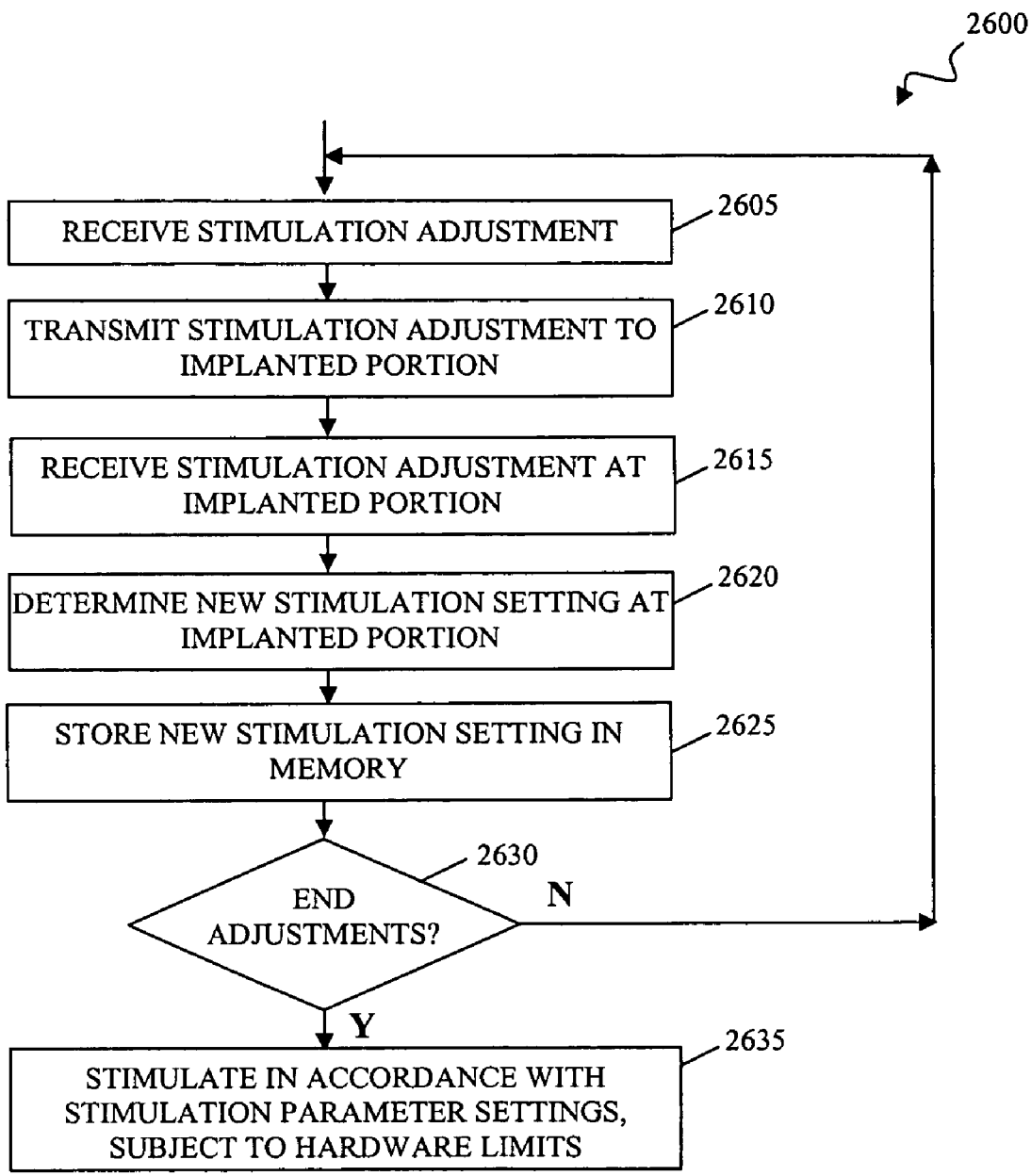
FIGS. 26, 27 show processes for controlling the stimulation of tissue using an implanted portion that includes one or more hardware limiters.

FIG. 26 shows a process 2600 for controlling the stimulation of tissue using an implanted portion that includes one or more hardware limiters that define the allowable values of one or more stimulation parameters. Process 2600 can be performed by a system for stimulating tissue (such as system 100) that includes a implanted portion such as electrical stimulator 2500 (FIG. 25).

The system performing process 2600 can receive one or more stimulation adjustments at 2605. The proposed changes can include a complete new value of a parameter setting and/or changes relative to one or more existing parameter settings (including a default setting). The proposed change(s) can impact one or more stimulation parameters, such as parameters 215, 220, 225, 230, 235, 240, 245, 255, 260, 265, 270, 275, 280, 285, 290 (FIGS. 2A, 2B). The stimulation adjustments can be received over a user interface such as user interface 115 (FIG. 1).

The system can transmit the proposed stimulation adjustment to an implanted portion of a device for stimulating tissue at 2605. If process 2600 is performed by a system such as system 100 (FIG. 1), processor 130 can direct data transceiver 120 to transmit the proposed stimulation adjustment to implanted portion 105 over data link 140.

The implanted portion of the system performing process 1400 can receive the proposed stimulation adjustment at 2615. For example, an implanted portion such as stimulator 2500 can receive the stimulation adjustment over data transceiver 315 (FIG. 25).

The implanted portion of the system performing process 2600 can determine a new stimulation setting at the implanted portion at 2620. The determination of a new setting can depend on the nature of the stimulation adjustment. If the system performing process 2600 includes a stimulator 2500, the new stimulation setting can be determined by electrical circuitry 310 (FIG. 25).

The system can also store the new stimulation setting in a memory at the implanted portion at 2625. This storage can include a write operation to one or more memory devices over a memory interface. If the system includes a stimulator 2500, the new stimulation setting can be stored at memory 325 by electrical circuitry 310 (FIG. 25).

The system performing process 2600 can also determine if adjustments are to end at 2630. This determination can be made based on a number of different factors including the existence of unset stimulation parameters, user input indicating that adjustments are to end, or a lack of user input over time.

If the system determines that adjustments are not going to end, then the system can receive additional proposed stimulation adjustment(s) at 2605.

If the system determines that adjustments are indeed to end, then the system can, subject to the hardware limits, stimulate in accordance with the existing stimulation parameter settings at 2635. Since the hardware limiters define the allowable values of one or more stimulation parameters, any parameter setting that would otherwise yield stimuli with stimulation parameters beyond those possible values is moderated by the hardware limiters. In particular, stimuli with stimulation parameters beyond those possible values are not actually received by tissue. Rather, the hardware limiters limit the stimuli to stimulation parameters within the range of possible values independently of other elements of electrical circuitry 310.

Figure 27:
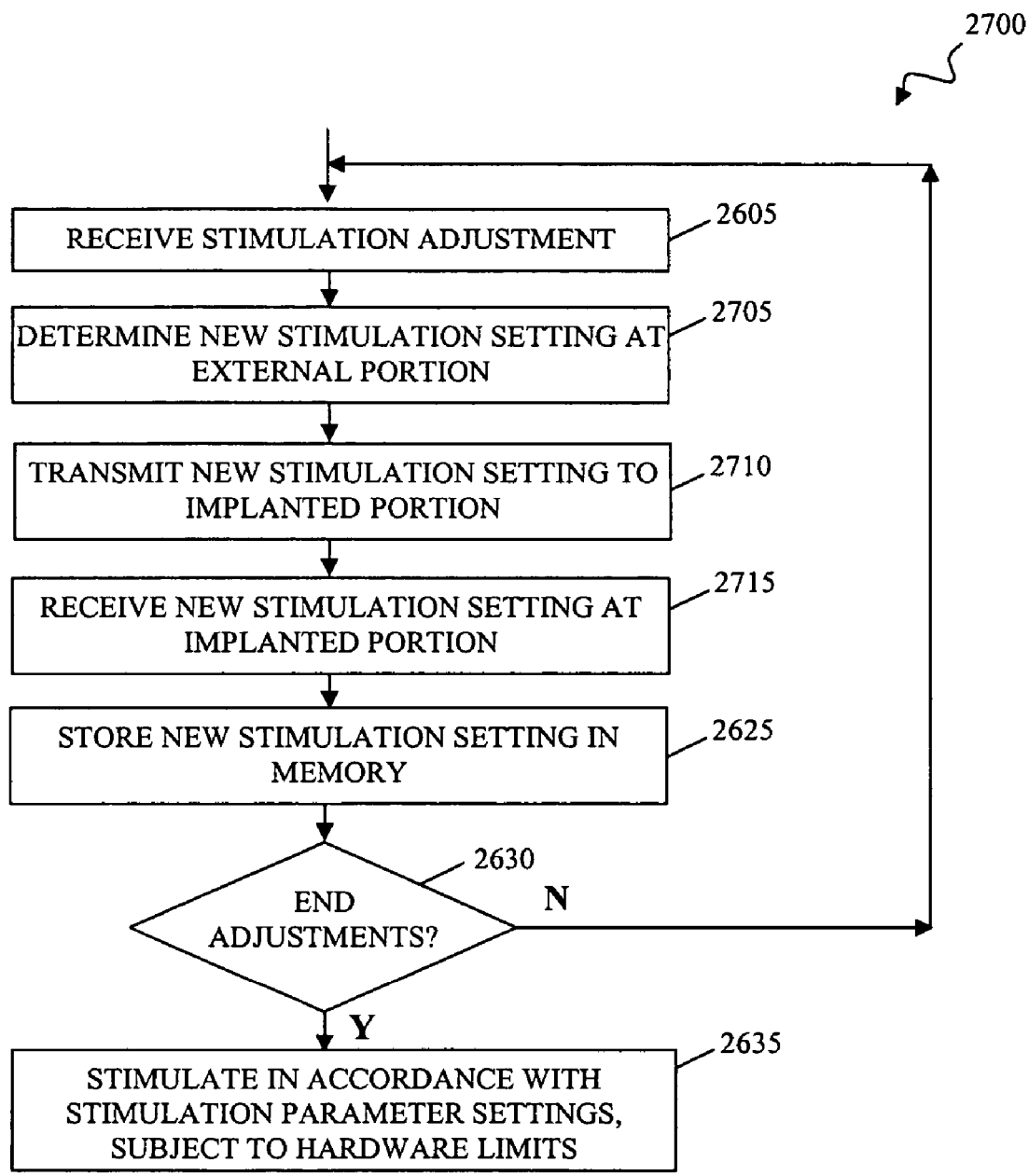

FIG. 27 shows a process 2700 for controlling the stimulation of tissue using an implanted portion that includes one or more hardware limiters that define the allowable values of one or more stimulation parameters. Process 2700 can be performed by a system for stimulating tissue (such as system 100) that includes a implanted portion such as electrical stimulator 2500 (FIG. 25).

The system performing process 2700 can receive one or more stimulation adjustments at 2605. The system can also determine a new stimulation setting at the external portion at 2705. The determination of a new setting can depend on the nature of the stimulation adjustment. The determination of a new setting can depend on the nature of the stimulation adjustment. For example, if the stimulation adjustment is a complete new value of a parameter setting, determining the new setting need only include identifying which parameter is to be set to the new setting. On the other hand, if the stimulation adjustment is a change relative to a existing parameter setting, determining the new setting can also include computing the new setting based on the existing parameter setting and the appropriate change. If the system performing process 2700 is system 100, the new stimulation setting can be determined by processor 130 (FIG. 1).

The system can also transmit the appropriate adjustment to an implanted portion at 2710. If process 2700 is performed by a system such as system 100 (FIG. 1) that includes a stimulator 2500 (FIG. 25), processor 130 can direct data transceiver 120 to transmit the new stimulation setting to stimulator 2500 over data link 140.

The system performing process 2700 can receive the new stimulation setting at an implanted portion at 2715. If the system performing process 2700 includes a stimulator 2500, transceiver 315 can receive the new stimulation setting (FIG. 25).

The system can also store the new stimulation setting in a memory at the implanted portion at 2625 and determine if adjustments are to end at 2630.

If the system determines that adjustments are not going to end, then the system can receive additional proposed stimulation adjustment(s) at 2605. If the system determines that adjustments are indeed to end, then the system can, subject to the hardware limits, stimulate in accordance with the existing stimulation parameter settings at 2635. The hardware limits are independent of the other elements and boundaries found in electrical circuitry 310.

Figure 28:
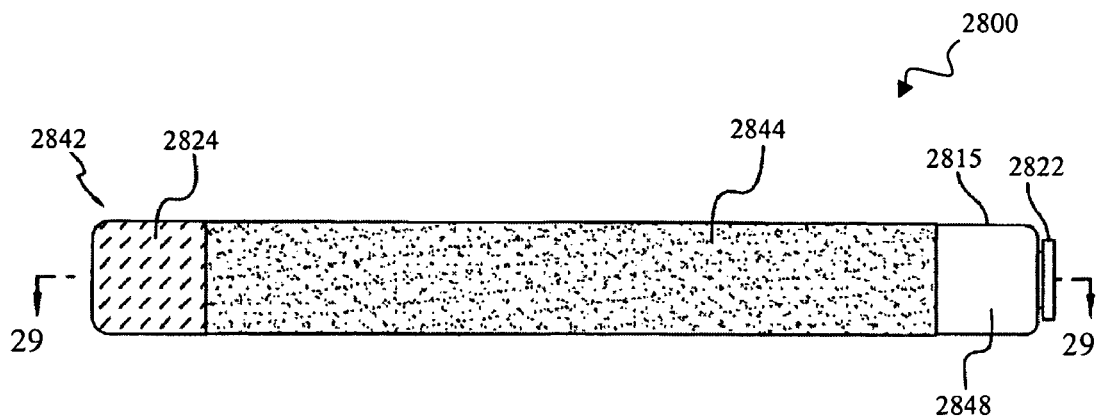
FIGS. 28-30 show another implementation of an implanted portion of the system of FIG. 1.
Figure 29:
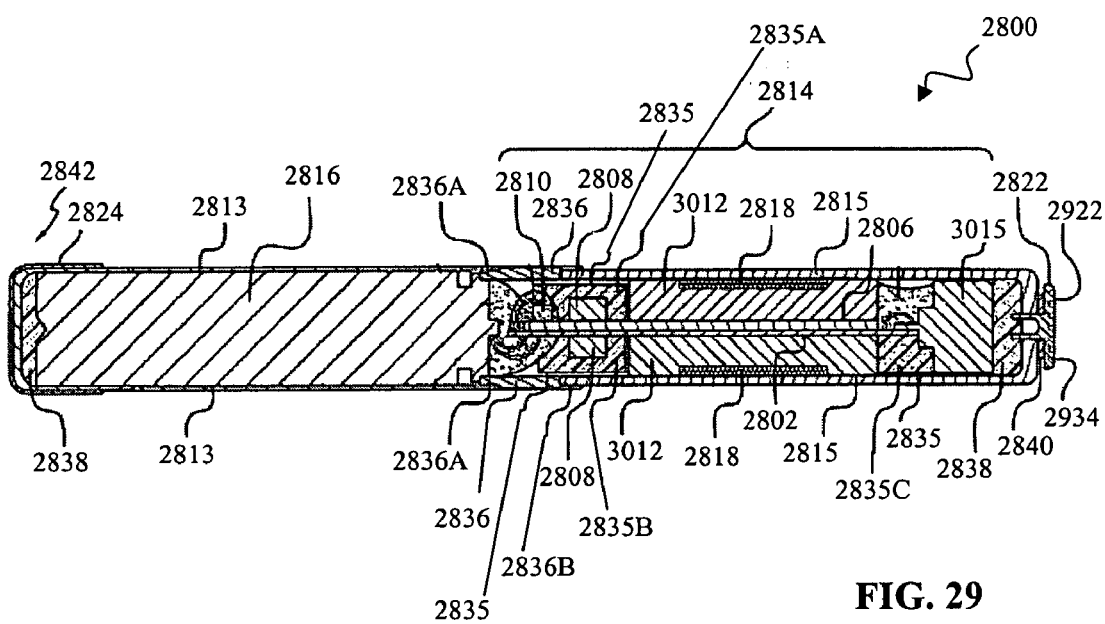
Figure 30:
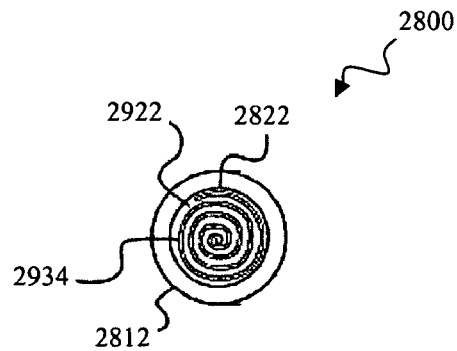

FIGS. 28, 29, and 30 show another implementation of implanted portion 105, namely a stimulator 2800. In particular, FIG. 28 shows a side view of stimulator 2800, FIG. 29 shows a sectional view of stimulator 2800 along the line 29-29 in FIG. 28, and FIG. 30 shows an end view of stimulator 2800.

Stimulator 2800 includes electrodes 2822 and 2824, a power source 2816, electronic subassembly 2814, and a case 2812. Electrode 2822 is an active/stimulating electrode whereas electrode 2824 is an indifferent/reference electrode. Electrodes 2822 and 2824 can be made from any of the materials discussed above.

Power source 2816 provides power for the deliver of electrical stimuli to tissue through electrodes 2822 and 2824. Power source 2816 can be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is placed in the middle of the long, thin-rod shape of the microstimulator), a bioenergy power source (where a chemical reaction provides an energy source), a fuel cell (much like a battery, but does not run down or require recharging, but requires only a fuel), a bioelectrical cell (where two or more electrodes use tissue-generated potentials and currents to capture energy and convert it to useable power), an osmotic pressure pump (where mechanical energy is generated due to fluid ingress), or the like.

When power source 2816 is a battery, it can be a lithium-ion battery or other suitable type of battery. When power source 2816 is a rechargeable battery, it can be recharged from an external system through a power link such as power link 145 (FIG. 1). One type of rechargeable battery that can be used is disclosed in International Publication WO 01/82398 A1, published Nov. 1, 2001, and/or WO 03/005465 A1, published Jan. 16, 2003, the contents of both of which are incorporated herein by reference. Other battery construction techniques that can be used to make power source 2816 include those shown, e.g., in U.S. Pat. Nos. 6,280,873; 6,458,171, and U.S. Publications 2001/0046625 A1 and U.S. 2001/0053476 A1, the contents of all of which are also incorporated herein by reference. Recharging can be performed using an external charger.

Electronic subassembly 2814 includes a coil 2818 and a stimulating capacitor 3015. Electrode 2822 is coupled to electronic subassembly 2814 through stimulating capacitor 3015. The coil 2818 can receive power for charging power source 2816 using power received over power link 145 (FIG. 1).

Electronic subassembly 2814 can also include circuitry for stimulation, battery charging (when needed), telemetry, production testing, and behavioral control. The stimulation circuitry can be further divided into components for high voltage generation, stimulation phase current control, recovery phase current control, charge balance control, and over voltage protection circuitry. The telemetry circuitry can be further divided into an OOK receiver, FSK receiver, and FSK transmitter. The behavioral control circuitry can be further divided into components for stimulation timing, high voltage generation closed loop control, telemetry packet handling, and battery management. In addition to these functions, there is circuitry for reference voltage and reference current generation, system clock generation, and Power-On Reset (POR) generation.

In operation, charging circuitry within electronic subassembly 2814 can detect the presence of an external charging field. Upon detection, stimulator 2800 can receive a telemetry message and recharge power source 2816, as necessary. The electronic subassembly 2814 can measure a rectified voltage during recharging and transmit the measured voltage value to an external device over a data link such as link 140 (FIG. 1). Battery voltage measurements can be made at times when stimulation pulses are not being delivered. U.S. Pat. No. 6,553,263, incorporated herein by reference, describes charging technology that also can be used.

When power source 2816 used within stimulator 2800 is something other than a rechargeable battery, e.g., a primary battery and/or one of the alternative power sources described previously, then the electronic subassembly 2814 can be modified appropriately to interface with, control and/or monitor whatever power source is used. For example, when power source 2816 comprises a primary battery, electronic subassembly 2814 can be simplified to include only monitoring circuitry and exclude charging circuitry. Such monitoring circuitry can provide status information regarding how much energy remains stored within the primary battery to provide the physician and/or patient an indication of the remaining life of the battery.

As another example, when power source 2816 used within stimulator 2800 is a super capacitor used in combination with a primary battery and/or a rechargeable battery, electronic subassembly 2814 can use the charge stored on the super capacitor to power stimulator 2800 during times of peak power demand. Such times include times when telemetry signals are being transmitted from stimulator 2800 to one or more external device(s), or when the amplitude of the stimulation pulses has been programmed to be relatively high. When used in combination with a rechargeable battery, electronic subassembly 2814 can use the charge stored on the super capacitor to recharge the rechargeable battery or to power stimulator 2800 at times of high power demand.

Electronic subassembly 2814 can also include protection circuitry to act as a failsafe against battery over-voltage. A battery protection circuit can continuously monitor a battery's voltage and electrically disconnect the battery if its voltage exceeds a preset value.

Electronic subassembly 2814 can also include a memory and a processor and/or other electronic circuitry that allow it to generate stimulating pulses that are applied to a patient through electrodes 2822 and 2824 in accordance with logic located within the electronic subassembly 2814. The processor and/or other electronic circuitry can also control data communication with an external portion such as external portion 110 (FIG. 1). The processor and/or other electronic circuitry can allow stimulator 2800 to perform processes described above in FIGS. 14-24.

Electronic subassembly 2814 can also include a panel 2802, integrated circuitry 2806, capacitors 2808, diodes 2810, and two ferrite halves 3012. The arrangement of these components in electronic subassembly 2814 is described in U.S. patent Publication Ser. No. 2005/0021108, the contents of which are incorporated herein by reference.

Electronic subassembly 2814 can also include a hardware limiter such as hardware limiter 2505 (FIG. 25). The hardware limiter can allow stimulator 2800 to perform processes described above in FIGS. 26, 27.

Case 2812 can have a tubular or cylindrical shape with an outer diameter greater than about 3.20 mm and less than about 3.7 mm. For example, case 2812 can have an outer diameter of about 3.30 mm. Case 2812 can have a inner diameter that encloses electronic subassembly 2814 of greater than about 2.40 mm and less than about 2.54 mm. Case 2812 can have a inner diameter that encloses power source of greater than about 2.92 mm and less than about 3.05 mm. The length of case 2812 can be less than about 30 mm, and less than about 27 mm. The portion of case 2812 that encloses electronic subassembly 2814 can be less than about 13.00 mm in length. The portion of case 2812 that encloses power source 2816 that encloses power source 2816 can be about 11.84 mm in length. These dimensions are only examples and can change to accommodate different types of batteries or power sources. For example, stimulator 2800, instead of being cylindrically shaped, can have a rectangular or ovoid cross section. Case 2812 can be Magnetic Resonance Imaging (MRI) compatible.

Case 2812 is sealed to protect electrical components inside stimulator 2800. For example, case 2812 can be hermetically-sealed and made from two cylindrical cases, namely, a titanium 6/4 case 2813 and a zirconia ceramic case 2815. Other materials and shapes for the housing can also be used. A titanium 6/4 or other suitable connector 2836 can be brazed with a titanium nickel alloy (or other suitable material) to ceramic case 2815 for securing the mating end of titanium case 2813. A connector 2836 has an inside flange 2836A and an outside flange 2836B which serve to "self center" the braze assembly. Before inserting the subassembly and before securing the mating ends, conductive silicone adhesive 2838 can be applied to the inside end of the ceramic shell as well as to the inside end of the titanium shell. A molecular sieve moisture getter material 2835 is also added to areas 2835A, 2835B, and 2835C (FIG. 29) before the brazing process.

The "spiral" self centering button electrode 2822 can be made from titanium 6/4 or other suitable material and plated with an iridium coating or other suitable conductive coating. An end view of electrode 2822 is shown in FIG. 30. A spiral groove 2924 can be made in stimulating surface 2922 of the electrode 2822. Other groove shapes, such as a cross hatch pattern or other patterns can also be used to increase the conductive surface area 2922 of electrode 2822.

The sharp edges in groove 2924 can force a more homogeneous current distribution over the surface 2922 and decrease the likelihood of electrode corrosion over time by reducing current density along the sharp groove edges. A tool made in the shape of a trapezoid or similar shape can be used to cut the groove 2924 into a spiral or other shape. Other devices for cutting the groove 2924 can be used such as, e.g., ion beam etching.

The button electrode 2822 can act as active or stimulating electrode. A titanium/nickel alloy 2840 or other suitable material can be used to braze the button electrode 2822 to the zirconia ceramic case 2815. An end view of the stimulator 2800 is shown in FIG. 30 where the end view of the stimulating "spiral" button electrode 2822 can be seen. The end 2842 of the titanium shell 2813 can be plated with an iridium coating (other suitable conductive coating can be applied), which plated area becomes the indifferent iridium electrode 2824.

FIG. 28 shows a top view of stimulator 2800 with the external coatings depicted. A type C parylene or other suitable electrically insulating coating can be applied to the shaded area 2844, e.g., by standard masking and vapor deposition processes. The zirconia ceramic case is left exposed in area 2848 and the iridium electrode 2824 is shown on the end 2842 of the titanium case 2813.

U.S. Pat. No. 6,582,441, incorporated herein by reference, describes a surgical insertion tool which can be used for implanting stimulator 2800. The procedures taught in the '441 patent for using the tool and associated components can be used for implanting and extracting stimulator 2800. The surgical insertion tool described in the '441 patent facilitates the implantation of stimulator 2800 in a patient so that stimulating electrode 2822 is proximate to a nerve site (e.g., near the pudendal nerve for treating patients with urinary urge incontinence). The distance between electrode 2822 and the nerve site can be, for example, less than 1-2 mm.

Other implantation procedures exist relating to the specific area to be stimulated. The stimulator 2800 can also be implanted in other nerve sites relating to preventing and/or treating various disorders associated with, e.g., prolonged inactivity, confinement or immobilization of one or more muscles and/or as therapy for various purposes including paralyzed muscles and limbs, by providing stimulation of the cavernous nerve(s) for an effective therapy for erectile or other sexual dysfunctions, and/or by treating other disorders, e.g., neurological disorders caused by injury or stroke.

A number of implementations have been described. Nevertheless, it will be understood that various modifications may be made. For example, a system for stimulating tissue need not include an implanted portion that stimulates tissue but rather can include an external stimulator. An implanted portion can include one or more sensing devices that respond to one or more conditions in the body.

An implanted portion can control the stimulation of tissue based on its own operational status. For example, the implanted portion can determine whether or not it is currently stimulating tissue and then reject an adjustment itself. The implanted portion can then inform the external portion of the rejection. The external portion can convey the rejection to the user.

Other implementations are within the scope of the following claims.

What is claimed is:

1. An apparatus comprising:
an implantable stimulation device to elicit a response in a tissue by delivering one or more stimuli, the stimulation device including
a stimulus delivery element to deliver the one or more stimuli to elicit the response;
a memory to store a range value identifying a range of values of a stimulation parameter relative to a first value; and
a controller to control delivery of the one or more stimuli by the stimulus delivery element in accordance with the range value,
the stimulation parameter characterizing the one or more stimuli to be delivered by the stimulation device; and
a user interface configured to receive a proposed change to the stored range value.

2. The apparatus of claim 1, wherein the first value comprises a default value of the stimulation parameter.

3. The apparatus of claim 1, wherein the range value identifies the range of values by identifying a range of excluded values of the stimulation parameter.

4. The apparatus of claim 1, wherein the range of values comprises a range of allowable values of the stimulation parameter.

5. The apparatus of claim 1, wherein the range of values comprises a group of discrete allowable values of the stimulation parameter.

6. The apparatus of claim 1, wherein the first value comprises a midpoint of the range identified by the range value.

7. The apparatus of claim 1, wherein the first value comprises a boundary of the range identified by the range value.

8. The apparatus of claim 1, wherein the stimulation parameter characterizes an electrical signal delivered to stimulate the tissue.

9. The apparatus of claim 8, wherein the stimulation parameter characterizes one or more of a primary pulse amplitude, a primary pulse duration, a delay between a primary pulse and a secondary pulse, a secondary pulse amplitude, a secondary pulse duration, a period, a primary pulse shape, and a secondary pulse shape.

10. The apparatus of claim 1, wherein the stimulation parameter characterizes a bolus of chemical delivered to stimulate the tissue.

11. The apparatus of claim 1, wherein the stimulus delivery element comprises an electrode to deliver electrical stimuli to elicit the response.

12. The apparatus of claim 1, wherein the stimulus delivery element comprises a drug delivery device to deliver a chemical stimulus to elicit the response.

13. The apparatus of claim 1, wherein the controller comprises a data processing device to control the delivery of the one or more stimuli in accordance with logic of a set of machine-readable instructions.

14. The apparatus of claim 1, further comprising a data receiver to receive data from an extracorporeal portion, the received data including the range value stored at the memory.

15. An apparatus comprising:
an implantable stimulation device configured to deliver one or more stimuli to elicit a response from a tissue, the stimulation device including
a stimulus delivery element configured to deliver the one or more stimuli to elicit the response;
a transceiver configured to exchange data with an extracorporeal device;
a controller configured to control delivery of the one or more stimuli by the stimulus delivery element in light of the data exchanged with the extracorporeal device; and
a hardware limiter configured to limit the range of a characteristic of the one or more stimuli to be delivered by the stimulus delivery element independently of the controller.

16. The apparatus of claim 15, wherein the hardware limiter comprises a voltage limiter to limit a primary pulse voltage amplitude.

17. The apparatus of claim 15, wherein the hardware limiter comprises a current limiter configured to limit a primary pulse current amplitude.

18. The apparatus of claim 15, wherein the hardware limiter comprises a charge limiter configured to limit a charge delivered during a primary pulse.

19. The apparatus of claim 15, wherein the hardware limiter comprises a power limiter configured to limit a power delivered during a primary pulse.

20. The apparatus of claim 15, wherein the hardware limiter comprises a dosage limiter configured to limit a dosage of a chemical delivered to stimulate a tissue.

21. The apparatus of claim 20, wherein the dosage limiter comprises: a flowmeter to measure the dosage delivered and generate a shut-off signal; and a valve to receive the shut-off signal and stop the delivery of the chemical.

22. A system for stimulating tissue, comprising:
an implanted portion including
a stimulator configured to elicit a response from tissue using a stimulus, and
a data transmitter configured to transmit, over a data link, data regarding whether the stimulator is active; and
an extracorporeal portion including
a data receiver configured to receive the data from the implanted portion over the data link,
a user interface configured to receive a proposed change to the stimulus from a user,
a processor configured to hinder the change to the stimulus when the data receiver receives data indicating that the stimulator is not currently active, and
a logic circuit to determine if the proposed change to the stimulus received from the user would increase the stimulation,
wherein the processor is configured to reject the change to the stimulus when the data receiver receives data indicating that the stimulator is not active and the logic circuit determines that the proposed change would increase the stimulation, and
wherein the processor is configured to allow the change to the stimulus when the logic circuit determines that the proposed change would not increase the stimulation irrespective of whether the implanted device is active or inactive.

23. The system of claim 22, wherein the processor is configured to reject the change to the stimulus when the data receiver receives data indicating that the stimulator is not active.

24. A method comprising:
receiving a stimulation adjustment at an extracorporeal portion of a system for stimulating tissue, the stimulation adjustment proposing a change to one or more aspects of a stimulus to be delivered by an implanted stimulation device to elicit a response from a tissue;
at the extracorporeal portion of the system for stimulating tissue, deciding whether the proposed stimulation adjustment is appropriate by determining if the proposed stimulation adjustment would yield a stimulation parameter outside a range of values of the stimulation parameter, the stimulation parameter characterizing the stimulus to be delivered by the implanted stimulation device;
at the extracorporeal portion, if the proposed stimulation adjustment is appropriate,
determining a setting for the stimulation parameter based on the proposed stimulation adjustment and
transmitting the stimulation parameter setting to the implanted stimulation device;
at the implanted stimulation device, receiving the stimulation parameter setting from the extracorporeal portion; and
at the extracorporeal portion, if the proposed stimulation adjustment is not appropriate,
automatically altering the proposed stimulation adjustment to a value within the range of values of the stimulation parameter.

25. The method of claim 24, wherein determining if the proposed stimulation adjustment is appropriate comprises:
retrieving a stored stimulation boundary from the implanted portion; and
determining if the proposed stimulation adjustment is within the boundary retrieved from the implanted portion.

26. The method of claim 24, wherein determining if the proposed stimulation adjustment is appropriate comprises:
accessing a range value identifying a range of values of a stimulation parameter relative to a first value, the stimulation parameter characterizing the stimulus to be delivered by the stimulation device; and
determining if the proposed stimulation adjustment is within the range identified by the range value.

27. The method of claim 24, wherein transmitting the stimulation parameter setting to the implanted stimulation device comprises transmitting an incremental or decremental change to the stimulation parameter setting.

28. A method comprising:
at an extracorporeal portion of a system for delivering a stimulus to elicit a response from a tissue, comparing a stimulation parameter that would be yielded by a proposed adjustment to the stimulation parameter to a range of values of the stimulation parameter, the stimulation parameter characterizing the electrical signal to be delivered by an implanted portion of the system;
determining, based on the comparison, that the proposed adjustment is inappropriate if the proposed adjustment would violate a boundary on the range of values; and
accommodating the proposed stimulation adjustment by changing a setting of the stimulation parameter to the violated boundary.

29. The method of claim 28, wherein accommodating the proposed stimulation adjustment comprises transmitting the setting of the stimulation parameter from the extracorporeal portion to the implanted portion.

30. The method of claim 28, wherein accommodating the proposed stimulation adjustment comprises incrementing or decrementing the setting of the stimulation parameter to the violated boundary.

31. The method of claim 28, wherein accommodating the proposed stimulation adjustment comprises transmitting a revised stimulation adjustment from the extracorporeal portion to the implanted portion.

32. A method comprising:
   receiving, at an extracorporeal device, a proposed adjustment to a stimulus to be delivered by an implanted device, the stimulus to elicit a response from a tissue;
   determining whether the implanted device is active;
   determining whether the proposed adjustment would increase the stimulation provided by the stimulus; and
   if the implanted device is not active, rejecting the adjustment to leave the stimulus unchanged if the stimulation would be increased, but if the stimulation would not be increased, then allowing the proposed adjustment irrespective of whether the implanted device is active or inactive.

* * * * *